(12) United States Patent
Hamilton

(10) Patent No.: US 11,815,449 B2
(45) Date of Patent: Nov. 14, 2023

(54) AGRICULTURAL CONDITION DETERMINATION

(71) Applicant: CSBP Limited, Kwinana (AU)

(72) Inventor: Douglas Hamilton, Bicton (AU)

(73) Assignee: CSBP Limited, Kwinana (AU)

( * ) Notice: Subject to any disclaimer, the term of this patent is extended or adjusted under 35 U.S.C. 154(b) by 205 days.

(21) Appl. No.: 17/435,963

(22) PCT Filed: Mar. 5, 2019

(86) PCT No.: PCT/AU2019/050186
§ 371 (c)(1),
(2) Date: Sep. 2, 2021

(87) PCT Pub. No.: WO2019/169434
PCT Pub. Date: Sep. 12, 2019

(65) Prior Publication Data
US 2022/0146409 A1 May 12, 2022

(30) Foreign Application Priority Data
Mar. 5, 2018 (AU) .................... 2018900706

(51) Int. Cl.
*G01N 21/31* (2006.01)
*G01J 3/02* (2006.01)

(52) U.S. Cl.
CPC .......... *G01N 21/31* (2013.01); *G01J 3/0291* (2013.01); *G01N 2201/022* (2013.01)

(58) Field of Classification Search
CPC . G01N 21/31; G01N 2201/022; G01J 3/0208; G01J 3/0229; G01J 3/0232; G01J 3/0256; G01J 3/0264; G01J 3/027; G01J 3/0272; G01J 3/0291; G01J 3/0297; G01J 3/14; G01J 3/18; G01J 3/42; G01J 3/502
See application file for complete search history.

(56) References Cited

U.S. PATENT DOCUMENTS 6,393,927 B1   5/2002   Biggs et al.
6,512,577 B1 * 1/2003   Ozanich ............... G01J 3/0224
                                                    356/402
6,845,326 B1   1/2005   Panigrahi et al.
(Continued)

OTHER PUBLICATIONS

Extended European Search Report issued by EPO in connection with EP application 19763632.7 dated Oct. 12, 2022.
(Continued)

*Primary Examiner* — Hina F Ayub
(74) *Attorney, Agent, or Firm* — Levenfeld Pearlstein, LLC

(57) ABSTRACT

Apparatus for determining an agricultural condition in an agricultural environment, the apparatus including one or more processing devices configured to acquire spectral data by measuring sample radiation at least one of reflected from and transmitted through an agricultural sample obtained from the agricultural environment, use the spectral data and at least one computational model to determine an agricultural condition, the computational model embodying relationships between the spectral data and different agricultural conditions and use the agricultural condition to determine an indicator indicative of at least one of: the agricultural condition and an intervention to improve the agricultural condition.

12 Claims, 12 Drawing Sheets

(56) References Cited

U.S. PATENT DOCUMENTS

| | | | |
|---|---|---|---|
| 2001/0036295 | A1 | 11/2001 | Hendrickson et al. |
| 2004/0021077 | A1 | 2/2004 | Ambuel |
| 2014/0012732 | A1 | 1/2014 | Lindores |
| 2016/0299062 | A1 | 10/2016 | Marbach |
| 2017/0160131 | A1 | 6/2017 | Goldring et al. |
| 2017/0205338 | A1 | 7/2017 | Coates |
| 2017/0292908 | A1 | 10/2017 | Wilk et al. |
| 2017/0356847 | A1* | 12/2017 | Willuweit .......... G01J 3/0291 |
| 2018/0035605 | A1 | 2/2018 | Guan et al. |

OTHER PUBLICATIONS

Written Opinion issued by ISA/AU in connection with PCT/AU2019/050186 dated May 22, 2019.

International Search Report issued by ISA/AU in connection with PCT/AU2019/050186 dated May 22, 2019.

Chlorophyll Meter SPAD-502Plus, A lightweight handheld meter for measuring the chlorophyll content of leaves without causing damage to plants, Konica Minolta, 2009.

GrainSense—A laboratory in the hands of every farmer, 2018. https://web.archive.org/web/20181108141015/https:/www.grainsense.com/.

World's Smartest Sensor With our award-winning technology you can reach the next level, Spectral Engines, 2017, https://web.archive.org/web/20171101224658/https:/www.spectralengines.com/.

BaySpec, 2017, https://web.archive.org/web/20171214213431/http:/www.bayspec.com/.

Viavi, 2017, https://web.archive.org/web/20170927203946/http:/www.viavisolutions.com/en-us.

Si-Ware Systems is a fabless semiconductor company that is fostering silicon innovation, Si-Ware Systems, 2018, http://web.archive.org/web/20180219204021/http:/www.si-ware.com/.

Zeiss Deutschland, 2017, https://web.archive.org/web/20170713195017/https:/www.zeiss.de/corporate/home.html.

BASF Deutschland, 2017, https://web.archive.org/web/20171121162123/https:/www.basf.com/de/de.html.

Yara Knowledge grows, 2017, http://web.archive.org/web/20171230171311/http:/yara.com/.

Instant Chemical Characterisation Know your crop, Rapid Phenotyping, 2018, http://web.archive.org/web/20180203094540/http:/rapidphenotyping.com/.

Panorama Synergy, 2014, https://web.archive.org/web/20140314180429/https:/panoramasynergy.com/irm/content/ default.aspx.

\* cited by examiner

AGRICULTURAL CONDITION DETERMINATION

BACKGROUND OF THE INVENTION

The present invention relates to a method and apparatus for determining an agricultural condition in an agricultural environment, and in one particular example, for determining an agricultural condition to allow recommendations to be made to improve agricultural environment productivity. The present invention also relates to a spectrometer, and, in one particular example, to a spectrometer suitable for measuring spectral data from a sample in an agricultural environment.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Growers need a timely and accurate understanding of crop and pasture nutrient levels in order to optimise fertiliser application decisions throughout a crop or pasture's growth stages. In this regard, nitrogen is widely considered to be the most critical nutrient for overall plant growth and health, and is a key nutrient managed by many growers during the season to optimise yield outcomes. Where crops are not irrigated, the level of rainfall experienced during a season is one of the critical factors impacting additional nitrogen application decisions in season. To optimise plant uptake of nitrogen and adjust to match changing yield expectations, ideally this nitrogen should be applied just prior to a rainfall event. Where crops are irrigated, timing nitrogen applications more precisely is also a decision that could be better informed by real time analysis. In both irrigated and non-irrigated contexts, nitrogen applications represent a significant input cost that growers prefer to optimise to meet profit and environmental impact objectives. When applying nitrogen, it is also important to understand the levels of other key nutrients available to the plant, including potassium, sulphur and phosphorous, so that the appropriate balance of nutrients is achieved. For example, there is no point in applying additional nitrogen if potassium is also limited in its availability to the plant.

A number of different approaches exist for measuring nitrogen levels in growing crops, including using laboratory testing and normalized difference vegetation index (NDVI) based imaging. However, these approaches are generally unsuitable for guiding fertiliser application or other interventions. For example, lab testing tends to be laborious and untimely, whilst NDVI imaging is insufficiently precise to make decisions on significant fertiliser investment or other interventions, such as application of other treatments, timing of irrigation, or the like. Additionally, existing nitrogen sensors do not have the capability to detect other nutrients such as potassium, sulphur and phosphorous, meaning laboratory testing is the only mechanism available for monitoring these nutrients.

SUMMARY OF THE PRESENT INVENTION

In one broad form, an aspect of the present invention seeks to provide an apparatus for determining an agricultural condition in an agricultural environment, the apparatus including one or more processing devices that: acquire spectral data by measuring sample radiation at least one of reflected from and transmitted through an agricultural sample obtained from the agricultural environment; use the spectral data and at least one computational model to determine an agricultural condition, the computational model embodying relationships between the spectral data and different agricultural conditions; and, use the agricultural condition to determine an indicator indicative of at least one of: the agricultural condition; and, an intervention to improve the agricultural condition.

In one embodiment the at least one computational model is derived from reference spectral data measured for one or more reference agricultural samples from reference agricultural environments having known reference agricultural conditions.

In one embodiment the at least one computational model is derived by applying machine learning to the reference spectral data.

In one embodiment the one or more processing devices: determine at least one metric associated with the agricultural environment; and, apply the at least one metric to the at least one computational model.

In one embodiment the one or more processing devices determine the at least one metric using at least one of: at least one parameter; and, the spectral data.

In one embodiment the at least one metric relates to a constituent of the agricultural sample and the at least one metric is determined at least in part using the spectral data.

In one embodiment the at least one metric corresponds to an intensity of sample radiation at one or more selected wavelengths.

In one embodiment the at least one parameter is determined by at least one of: using user input commands; using sensor data received from one or more sensors; retrieving the at least one parameter from a stored agricultural environment record; retrieving the at least one parameter from a remote data store; and, retrieving the at least one parameter from a geographic information system (GIS).

In one embodiment the at least one parameter includes at least one of: a sample parameter including at least one of: a sample type; a sample variety; a sample nutrient status; a sample location; a sample growth stage; a sample growth history; and, a sample target yield; an agricultural environment parameter including at least one of: an agricultural environment location; intervention details; a crop history; a target yield or yield potential; biomass development; vegetation indices; soil indices; soil parameters including at least one of: pH; organic carbon levels; particle size; water holding capacity; and, soil nutrient levels; climate parameters including at least one of: temperature; rainfall; humidity; wind; and, sunlight levels; and, disease and pest incidences.

In one embodiment the one or more processing devices select one of a plurality of models in accordance with at least one parameter.

In one embodiment the one or more processing devices: use the spectral data and a first computational model to determine at least one metric, the first computational model embodying relationships between the spectral data and at least one metric; and, use the at least one metric and a second computational model to determine the agricultural condition, the second computational model embodying relationships between the at least one metric and the agricultural condition.

In one embodiment the first computational model is a chemometric model and the second computational model is an agronomic model.

In one embodiment the chemometric model determines levels in the sample of at least one of: nitrogen; phosphorous; potassium; sulphur; copper; zinc; manganese; magnesium; iron; moisture; stress compounds; proteins; oils; starch; ammonium nitrogen; nitrate nitrogen; pH; and, organic carbon levels.

In one embodiment the one or more processing devices use the agricultural condition, at least one metric and a third computational model to determine the intervention, the third computational model embodying relationships between the agricultural condition, the at least one metric and one or more interventions.

In one embodiment the at least one computational model is derived from reference metrics associated with reference agricultural environments having known reference agricultural conditions.

In one embodiment the apparatus includes a spectrometer that: exposes the agricultural sample to illuminating radiation; and measures the sample radiation.

In one embodiment the apparatus includes a client device in communication with the spectrometer, wherein, in use: the spectrometer is used in the agricultural environment to: expose the agricultural sample to illuminating radiation; measure the sample radiation; and, generate spectral data indicative of the sample radiation; and, the client device: receives the spectral data from the spectrometer; and, displays the indicator.

In one embodiment the client device determines at least one parameter in accordance with at least one of: sensor data received from a sensor; and, user input commands;

In one embodiment the client device includes the one or more processing devices.

In one embodiment the client device is in communication with the one or more processing devices, and wherein the client device: transfers at least the spectral data to the one or more processing devices; and, receives the indicator from the one or more processing devices.

In one embodiment the client device: generates sample data indicative of the spectral data and at least one parameter; and, transfers the sample data to the one or more processing devices.

In one embodiment the client device at least partially controls the spectrometer.

In one embodiment the spectrometer includes a housing having: an enclosure containing: a radiation source that generates illuminating radiation; and, a sensor that senses sample radiation; a window in the enclosure to allow illuminating radiation and sample radiation to pass therethrough; a cover movably mounted to the enclosure to allow the cover to move between: an open position in which the window is exposed; and, a closed position in which the window is covered, wherein in use a sample is provided between the cover and window, allowing the measurement of sample radiation.

In one embodiment the cover at least one of: is aligned at least one of: substantially parallel to the window; substantially perpendicularly to the radiation source; and substantially perpendicularly to the sensor; and, moves in a direction substantially perpendicular to the window.

In one embodiment the housing includes a biasing mechanism that biases the cover into the closed position.

In one embodiment the housing includes an actuator to urge the cover into the open position.

In one embodiment the at least one of the enclosure and cover include a deformable material extending at least part way around the window when the cover is in the closed position to thereby prevent ingress of at least one of ambient radiation and contaminants.

In one embodiment the deformable material is a memory foam, rubber or polymeric material.

In one embodiment the cover includes an optical surface and wherein the spectral data is at least partially indicative of radiation reflected from the optical surface.

In one embodiment the optical surface is orientated at least one of: substantially parallel to the window; substantially perpendicularly to the radiation source; and substantially perpendicularly to the sensor.

In one embodiment the optical surface includes at least one of: a fluoropolymer; and, spectralon.

In one embodiment the cover includes an optical surface window that protects the optical surface.

In one embodiment the cover includes a sample biasing mechanism configured to urge the sample towards the window.

In one embodiment the cover includes: an outer cover configured to substantially surround the window; and, a spring mounted inner cover supporting an optical surface, wherein the inner cover is configured to urge the sample against the window.

In one embodiment the housing includes a handle configured to allow hand-held operation of the spectrometer.

In one embodiment the housing includes a mounting configured to allow the client device to be coupled to the housing.

In one embodiment the sample is at least one of: plant material; grain material; soil material; wheat; barley; canola; oats; rice; sorghum; and, grasses.

In one embodiment the agricultural condition is indicative of at least one of: a nutrient status; a nutrient concentration; a nutrient deficiency; a nutrient sufficiency; a nutrient toxicity; a plant health status; plant productivity; soil health; and, soil productivity.

In one embodiment the intervention includes at least one of: at least one action to improve the agricultural condition of the agricultural environment; and, a nutrient supplement recommendation to improve the agricultural condition of the agricultural environment.

In one embodiment the one or more processing devices use the agricultural condition to at least one of: update a stored agricultural environment record for the agricultural environment; determine future sampling locations; determine a variable rate technology (VRT) program; determine the intervention; determine an intervention program; determine an intervention efficacy; generate yield predictions; and, generate revenue predictions.

In one embodiment the one or more processing devices generate a representation of the indicator.

In one embodiment the representation includes a map of the agricultural environment and indications of at least one of: agricultural conditions; interventions; future sampling locations; and, predicted yields.

In one broad form, an aspect of the present invention seeks to provide a method of determining an agricultural condition in an agricultural environment, the method including, in one or more processing devices: acquiring spectral data by measuring sample radiation at least one of reflected from and transmitted through an agricultural sample obtained from the agricultural environment; using the spectral data and at least one computational model to determine an agricultural condition in the agricultural environment, the computational model embodying relationships between the spectral data and different agricultural conditions; and, using the agricultural condition to determine an indicator indicative of at least one of: the agricultural condition; and, an intervention to improve the agricultural condition.

In one broad form, an aspect of the present invention seeks to provide an apparatus for determining an agricultural condition in an agricultural environment, the apparatus including: a spectrometer that: exposes an agricultural sample obtained from the agricultural environment to illuminating radiation; measures sample radiation at least one of reflected from and transmitted through an agricultural sample; and, generates spectral data indicative of the measured sample radiation; a client device that: receives the spectral data from the spectrometer; and, transfers at least the spectral data; and, one or more processing devices that: receive the spectral data from the client device; use the spectral data and at least one computational model to determine an agricultural condition of the agricultural environment, the computational model embodying relationships between the spectral data and different agricultural conditions; and, use the agricultural condition to determine an indicator indicative of at least one of: the agricultural condition; and, an intervention to improve the agricultural condition.

In one broad form, an aspect of the present invention seeks to provide a method for determining an agricultural condition in an agricultural environment, the method including: using a spectrometer to: expose an agricultural sample obtained from the agricultural environment to illuminating radiation; measure sample radiation at least one of reflected from and transmitted through an agricultural sample; and, generate spectral data indicative of the measured sample radiation; using a client device to: receive the spectral data from the spectrometer; and, transfer at least the spectral data; and, using one or more processing devices that: receive the spectral data from the client device; use the spectral data and at least one computational model to determine an agricultural condition of the agricultural environment, the computational model embodying relationships between the spectral data and different agricultural conditions; and, use the agricultural condition to determine an indicator indicative of at least one of: the agricultural condition; and, an intervention to improve the agricultural condition.

In one broad form, an aspect of the present invention seeks to provide a spectrometer including a housing having: an enclosure containing: a radiation source that generates illuminating radiation; and, a sensor that senses sample radiation; a window in the enclosure to allow illuminating radiation and sample radiation to pass therethrough; a cover movably mounted to the enclosure to allow the cover to move between: an open position in which the window is exposed; and, a closed position in which the window is covered, wherein in use a sample is provided between the cover and window, allowing the measurement of sample radiation.

In one embodiment the cover at least one of: is aligned at least one of: substantially parallel to the window; substantially perpendicularly to the radiation source; and substantially perpendicularly to the sensor; and, moves in a direction substantially perpendicular to the window.

In one embodiment the housing includes a biasing mechanism that biases the cover into the closed position.

In one embodiment the housing includes an actuator to urge the cover into the open position.

In one embodiment the at least one of the enclosure and cover include a deformable material extending at least part way around the window when the cover is in the closed position to thereby prevent ingress of at least one of ambient radiation and contaminants.

In one embodiment the deformable material is a memory foam, rubber of polymer.

In one embodiment the cover includes an optical surface and wherein the spectral data is at least partially indicative of radiation reflected from the optical surface.

In one embodiment the optical surface is orientated at least one of: substantially parallel to the window; substantially perpendicularly to the radiation source; and substantially perpendicularly to the sensor.

In one embodiment the optical surface includes at least one of: a fluoropolymer; and, spectralon.

In one embodiment the cover includes an optical surface window that protects the optical surface.

In one embodiment the cover includes a sample biasing mechanism configured to urge the sample towards the window.

In one embodiment the cover includes: an outer cover configured to substantially surround the window; and, a spring mounted inner cover supporting an optical surface, wherein the inner cover is configured to urge the sample against the window.

In one embodiment the housing includes a handle configured to allow hand-held operation of the spectrometer.

In one embodiment the housing includes a mounting configured to allow the client device to be coupled to the housing.

It will be appreciated that the broad forms of the invention and their respective features can be used in conjunction and/or independently, and reference to separate broad forms is not intended to be limiting. Furthermore, it will be appreciated that features of the method can be performed using the system or apparatus and that features of the system or apparatus can be implemented using the method.

BRIEF DESCRIPTION OF THE DRAWINGS

Various examples and embodiments of the present invention will now be described with reference to the accompanying drawings, in which:—

DETAILED DESCRIPTION OF THE PREFERRED EMBODIMENTS

Figure 1:
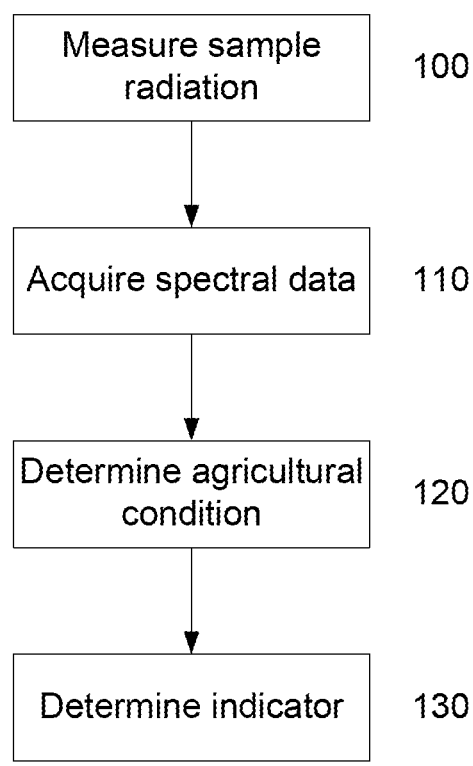
FIG. 1 is a flowchart of an example of a process for determining an agricultural condition in an agricultural environment.

An example of a process for determining an agricultural condition in an agricultural environment will now be described with reference to FIG. 1.

For the purpose of illustration, the term agricultural environment will be understood to include any location or situation in which cultivation is performed for the purpose of growing crops or other plants, or rearing of animals to provide food, fibre, and other products. However, the term is also intended to encompass the subsequent distribution of resulting products, and could therefore include a product supply chain through to an end product user.

The term agricultural sample refers to a sample collected from or within the agricultural environment, and could include samples obtained from soil, crops, plants, or the like. However, this is not intended to be limiting, and it will be appreciated that the techniques described herein could be more broadly applied to analysis of soil qualities and harvested products including fruit and vegetables, or the like.

The agricultural condition is understood to provide information regarding the current condition of either the agricultural sample or the environment from which the sample was taken. For example, the sample can include plant material grown in the agricultural environment, with the agricultural condition being indicative of the state of growth of the plant, such as the current plant health or yield. Alternatively, the sample could include a soil sample, in which case the agricultural condition is indicative of the constituents of the soil. However, this is not essential, and alternatively, the sample could be a plant, with the agricultural condition being indicative of the ability of the agricultural environment to support growth of the plant.

For the purpose of illustration, it is assumed that the process is performed at least in part using one or more electronic processing devices forming part of one or more processing systems, such as servers, which are in turn connected to one or more spectrometers, and optionally one or more client devices, such as mobile phones, portable computers or the like, via a network architecture, as will be described in more detail below. However, this is not intended to be limiting, and it will be appreciated that the one or more processing devices, could form part of a client device or other hardware, such as a spectrometer.

In this example, at step 100 sample radiation is measured, with the sample radiation being either reflected from or transmitted through the agricultural sample. The manner in which this is performed will vary depending on the preferred implementation and could involve using a spectrometer to expose an agricultural sample to illuminating radiation, with the spectrometer measuring the resulting sample radiation. Alternatively, this could involve using remote sensing, for example using sample radiation reflected from plants under ambient lighting conditions. It will be appreciated that the radiation can be of any appropriate form of electromagnetic radiation, and could include visible light, infrared radiation, combinations thereof, or the like and that the use of reflection or transmission will vary depending upon factors such as the nature of the sample and the manner in which the measurement is performed.

At step 110, the one or more processing devices acquire spectral data. The spectral data could be received directly from a measuring device, such as a spectrometer, or may be routed via one or more intermediate devices. In one preferred example, the spectral data is received from a client device, such as a mobile phone, in communication with the spectrometer. It will be appreciated however, that this is not essential and alternatively the spectral data could be acquired in other manners, such as retrieving the spectral data from a database or other suitable repository. Alternatively, the spectrometer could be integrated within the client device, in which case the spectral data will simply be received directly from the sensor.

The spectral data is typically indicative of at least the sample radiation, and optionally the illuminating radiation. The spectral data could include a full spectrum including an indication of an intensity of transmitted or reflected radiation at each of a plurality of wavelengths and/or could include semi processed data, for example indicative of the intensity of radiation at specific selected wavelengths.

At step 120, the one or more processing devices use the spectral data and at least one computational model to determine an agricultural condition in the agricultural environment. In this regard, the computational model(s) typically embodies relationships between the spectral data and different agricultural conditions and in one example is determined based on reference agricultural samples obtained from reference agricultural environments having a known reference agricultural conditions, as will be described in more detail below.

The nature of the computational model and the manner in which this is performed will vary dependent upon the preferred implementation method. For example, the computational model could directly relate spectral data to an agricultural condition. More typically however, the spectral data is used, optionally in conjunction with other information, to determine one or more metrics, which are then applied to the model to determine the agricultural condition. Thus, for example, the metrics could include spectral metrics indicative of the intensity of the sample radiation at specified wavelengths corresponding to absorption wavelengths of particular nutrients but could also include information regarding the sample or agricultural environment, including levels of rainfall, details of previous interventions, or the like, and further examples will be described in more detail below.

The agricultural condition is typically indicative of the agricultural condition of the sample itself, but alternatively can be indicative of an agricultural condition of the agricultural environment from which the sample is collected. Thus, for example, the sample could include a plant or crop with the agricultural condition corresponding to the condition of the soil or other substrate in which the plant is grown. This is particularly true for heavily controlled environments such as hydroponic systems, where the plants have unrestricted access to nutrients and or other constituents of the growing medium. However, in broader agricultural environments plants may not be able to access all nutrients in the growing medium, for example due to physical or chemical restrictions, such as compaction layers, low pH, barriers to root exploration, or the like. Accordingly, more typically the agricultural condition is indicative of the ability for the soil or substrate to supply nutrients to the plant or crop in sufficient quantities, or not, due to any physical or chemical limitations of a particular soil profile.

The determined agricultural condition could be indicative of the levels or concentrations of one or more different nutrients, and/or could include a recommendation, such as an indication of one or more nutrients that could be added to the agricultural environment, for example to improve agricultural conditions. It will be appreciated that this will vary depending upon the nature of the agricultural environment and the sample.

Once determined, the agricultural condition can be used to determine an indicator, indicative of either the agricultural condition and/or any recommended interventions or other recommendations. For example, if certain deficiencies are identified, such as a nitrogen deficiency, this could be used to recommend application of a nutritional supplement, such as a fertiliser. Alternatively, potassium deficiency may imply frost and pest vulnerability, which might be used to perform increased monitoring of the crop, potentially influencing the application of pesticides or the timing of harvesting.

The indicator can be used in a variety of ways, and could be displayed directly to a user, or used to update an agricultural record, allowing a record of changes in agricultural condition over time to be established. This can be used in conjunction with other information, such as details of applied treatments, crop yields, climate information, or the like, to track the agricultural condition and determine how this can be best controlled to achieve optimal yields and thereby returns on nutrient spend by the grower.

Accordingly, the above described process allows a sample, such as plant material, to be collected within the agricultural environment. The sample can be analysed locally using a spectrometer, which is typically portable and hand-held, or using other remote sensing modalities. Resulting spectral data can then be analysed locally, for example using a client device, or could be transferred to one or more other remote processing devices for analysis.

The analysis can be performed utilising a computational model, which enables an agricultural condition to be derived using the spectral data. The models could be stored locally on a client device, or other similar processing system, allowing the process to be performed in the agricultural environment, without requiring onward connectivity to other computers, which can be particularly important in remote environments. However, this is not essential and in other arrangements, the models might be hosted centrally by a server, which performs the analysis, uploading results to a client device as needed.

The agricultural condition can then be stored as part of an agricultural environment record, which can be used for a variety of purposes, such as to perform ongoing monitoring of changes in agricultural condition, and/or could be displayed directly to a user via the client device. This could be in the form of a simple indication of the agricultural condition, for example to indicate levels of nutrients or other sample constituents, but could also include more complex reporting, for example displaying results as part of a geographic information system (GIS) layer. In another example, this can include providing a recommendation for one or more treatments, such as a recommendation for fertilisers or other nutrient supplements that can be applied to the agricultural environment in order to enhance the environment for plant growth or the like. Similarly, recommendations could relate to other actions, such as recommendations for amounts and timing of irrigation, or the like.

Accordingly, it will be appreciated that this provides a mechanism for a farmer or other agricultural land user to rapidly understand the current agricultural condition of the agricultural environment, in turn allowing action to be taken to mitigate problems and enhance the agricultural condition. This is particularly important as there are a range of complex interactions that occur, for example between plant nutrients, and with the environment, that affect plant health and the productivity of the agricultural environment. As it can be difficult for farmers to understand these interactions, providing a system that can perform automatic analysis, presenting the results in a simple easy to understand manner, in real time, allows the farmer to allow better control over farming inputs and outputs. For example, ensuring key nutrients such are in balance in relation to one another in order to best understand the type of fertiliser treatments required in order to meet target yields.

A number of preferred features will now be described.

In one example, the at least one computational model is derived from reference spectral data measured for one or more reference agricultural samples from reference agricultural environments having known reference growing conditions. Thus, it will be appreciated that reference samples can be collected from multiple different reference environments with these being scanned using a spectrometer in order to determine reference spectral data. The reference spectral data is then correlated with known reference growing conditions in order to establish the computational model. It will be appreciated that this can be achieved using a similar process to that described above, with additional analysis of the agricultural environment to determine the reference agricultural conditions, for example through laboratory analysis, or the like.

The computational model can also be based on other metrics, such as parameters relating to the sample and/or agricultural environment, and examples of these will be described in more detail below.

Whilst derivation of the model could be performed manually utilising suitable statistical analysis, in practice the model is derived utilising a machine learning algorithm. In particular, this is typically performed by utilising the reference spectral data and known reference agricultural condition in order to train a computational model. The nature of the model and the training performed can be of any appropriate form and could include any one or more of decision tree learning, random forest, logistic regression, association or learning, artificial neuron networks, deep learning, inductive logic programming, support vector machines for regression, Lasso Regression, ridge and kernel ridge regression, ensemble methods, clustering, Bayesian networks, reinforcement learning, representation learning, similarity and metric learning, genetic algorithms, rule-based machine learning, learning classifier systems, or the like. As such schemes are known these will not be described in any further detail.

The manner in which the computational model is used will vary depending on the preferred implementation. In one particular example, as part of this process, the one or more processing devices operate to determine at least one metric and then apply the metric to the at least one computational model. In this example, the one or more metrics act as inputs into the model, enabling the model to calculate the agricultural condition. It will be appreciated from this that one or more of the metrics could be derived from the spectral data, and could include for example an indication of a reflection or transmission intensity at one or more particular wavelengths, corresponding to particular nutrients.

In addition to this, the metric could include one or more parameters relating either to the sample and/or the agricultural environment. The parameters could include sample parameters such as a sample type, a sample variety; a sample nutrient status, a sample location, a sample growth stage, a sample growth history, a sample target yield, or the like. The parameters may include an agricultural environment parameter, such as an agricultural environment location, intervention details, such as information regarding a type and timing of an intervention such as a disease or pest treatment programme, a crop history, a target yield, biomass development, vegetation indices or soil indices, or disease or pest indications. The parameters can include soil parameters such as a pH, organic carbon levels, particle size, water holding capacity or nutrient levels, which might be measured prior to planting, or during the growing season, depending on the particular implementation. The parameters could also include climate parameters including any one or more of temperature, rainfall, humidity, wind speed and wind direction, and sunlight levels, or the like. Thus, it will be appreciated that this allows the model to take into account additional variables, recognising for example that the level of nutrients in the soil may vary depending on factors, such as rainfall, the nature of the soil, or the like, as well as the relative concentration of different nutrients in the sample.

Such parameters could be determined in a wide variety of manners, depending upon the preferred implementation and the nature of the parameter. For example, the parameters could be determined based on user input commands provided via a client device, and/or could be based on sensor data received from one or more sensors, such as climate sensors, GPS or other positioning systems, remote sensing platform such as satellites, manned and unmanned aerial vehicles, or the like. Additionally, and/or alternatively, parameters could be retrieved from a stored agricultural environment record. In this regard, it will be appreciated that as some parameters may remain relatively constant over time, or only be measured once at the start of a growing season, in which case details of these may not need to be provided each time an agricultural condition assessment is to be performed. Thus, over a single growing season, the type and variety of the sample at a location will remain constant, allowing this information to be retrieved automatically from a record for the given sampling location. Similarly, a record could be defined for a region such as a field, with the variety of crop at different locations within the field being automatically determined by inheriting the information from a record for the field. It will be appreciated from this that in practice a farm could define the crops located within each field, with the identity of each sample being automatically determined based on a location of the sample within the farm.

Additionally, parameters could be retrieved from a remote data store, for example to allow parameters to be retrieved from third parties, such as obtaining climate data from a bureau of meteorology. Data can be retrieved from a GIS system, for example to retrieve soil and plant spectral indices and/or analysis obtained from processing spectral bands captured by remote sensing platforms, or radar backscatter used to measure biomass/plant density/leaf area indices. This information can also be used to provide a recommendation to the user in order to guide further sample collection. For example, the biomass measurements may highlight areas of low biomass, guiding the user to perform sample collection in those areas, in order to identify issues with the agricultural condition.

The manner in which the spectral data and other parameters are analysed will vary depending upon the preferred implementation. For example, this could involve having the processing devices select one of a plurality of models in accordance with one parameter, then using spectral data and other parameters as inputs into the model. Thus, for example, different models may be established for different sample types and/or varieties, with a respective one of the models being selected based on an indicated sample type or variety.

In one specific example, a first computational model is used to determine a metric, which is then applied to a second computational model to determine the agricultural condition. In this case, the first computational model typically embodies relationships between the spectral data and the metric, whilst the second computational model embodies relationships between the metric and the agricultural condition.

In one particular example, the first computational model can be a chemometric model, which relates spectral data to particular levels of nutrients or other sample constituents, such as levels of nitrogen, phosphorus, potassium, sulphur, copper, zinc, manganese, magnesium, iron, moisture, stress compounds such as such as ethylene, abscisic acid, salicylic acid, jasmonic acid, or the like, proteins, oils, starch, ammonium nitrogen, nitrate nitrogen, organic carbon levels, or the like. In this case, the second computational model is an agronomic model, which relates the sample levels to different growing conditions, and in particular nutrient deficiencies and/or a nutrient supplement recommendation. It will be appreciated that this allows different combinations of chemometric and agronomic models to be used in combination. For example, different chemometric models could be established for different plant varieties, with these being used with a single agronomic model to relate the determine level of nutrients in the plant to the agricultural condition of the soil.

The system could also use a third computational model to determine an intervention. In this instance, the third computational model typically considers the agricultural condition and at least one metric, with the computational model embodying relationships between the agricultural condition and the at least one metric and one or more interventions.

In one particular example, the metrics and measured nutrient levels forming part of the agricultural condition are used to determine a potential yield limitation, with this information then being used in conjunction with a target yield or other information to determine details of interventions that might be required. For example, the system can determine an expected yield loss based on the current agricultural condition, and then predict an improved yield that can be obtained by correcting for any nutritional or other deficiencies, for example by applying fertilisers or the like.

Types of metrics that can be taken into account in order to predict yield, include rainfall data, including year to date, forecasts and zones, soil productivity parameters obtained from soil tests, including the relative levels or nutrients, such as ammonium ($NH_4$), nitrate ($NO_3$), colwell potassium, colwell phosphorous, sulphur, copper, zinc, manganese, iron, calcium, magnesium, pH, electrical conductivity (EC), organic carbon (OC), texture & gravel percentages, phosphorous buffering index (PBI), cation exchange capacity (CEC), particle size distribution, soil depth, or the like. The metrics can include non-soil test parameters, such as a subjective soil productivity parameters based on agronomic knowledge and experience. For example based on a farmer/farm manager's knowledge judgement of how productive an area of a paddock is in their experience, compared to the rest of the paddock. The metrics can also include biomass development, including plant weight, growth stage, sowing date, tiller count and plant count/$m^2$, leaf area index (camera), vegetation indices, or the like. Additionally, this can take into account nutrient supply/availability to the plant, pre-seeding soil tests, in season plant test, season nutrient applications, details of previous crop rotations, or the like.

The system can then further predict a revenue based on the current and predicted improved yield, together with an associated cost of the intervention, allowing the farmer to make an informed decision regarding the benefit of applying the intervention. In particular, this can take into account a farmer's risk tolerance for nutrient investment as well as a current economic environment, such as last season's financial performance, current commodity prices, current intervention costs, or the like.

It will be further appreciated that as samples can be measured at a range of different locations within the agricultural environment, such guidance could be targeted, recommending different inventions in different parts of a farm, in order to optimise the yield profile.

As previously mentioned, the apparatus can include a client device, such as a smartphone, tablet, or the like, in communication with the spectrometer and the one or more processing devices. In this example, the spectrometer is used in the agricultural environment to expose the agricultural sample to illuminating radiation, measure the sample radiation and generate spectral data indicative of the sample radiation. The spectral data can then be transferred to the client device, which receives the spectral data and transfers this to the one or more processing devices. This allows communication between the spectrometer to be achieved using a short-range communications technique, such as Bluetooth or the like, with ongoing connectivity to the process device(s) being provided by the client device's existing communications system.

As part of this data collection process, the client device can collect additional information, such as one or more of the parameters outlined above. In this example, the client device determines at least one parameter, based on input commands and/or sensor data from onboard or connected sensors, generates sample data indicative of the spectral data and the at least one parameter and then transfers the sample data to the one or more processing devices, such as remote processing system or one or more locally housed processing modules. Thus, in this instance the client device acts to further facilitate data capture.

The client device can be used solely for the purpose of transferring data between the spectrometer and the processing device(s), such as remote processing system or one or more locally housed processing modules, but more typically can also be used for displaying results and/or controlling the spectrometer, for example to initiate the measurement process, and display the resulting agricultural condition, allowing a farmer or other user to leverage an existing client device to control the overall process.

This allows the sample collection and analysis to be performed in-situ, within the agricultural environment, with results being provided for immediate display to the user. This in turn allows a user to make an immediate decision regarding remedies, such as the application of fertilizer, treatments, or the like.

However, other arrangements could be used. For example, the functionality of the client device and spectrometer could be integrated into a single device, which in one example could be achieved through the use of a suitable optical arrangement that can use a smartphone camera in order to measure the sample radiation. Similarly, the models can be incorporated into the client device, avoiding the need for remote processing devices.

The spectrometer can be of any appropriate form, but in one example includes an enclosure containing a radiation source, such as a lamp or laser, that generates illuminating radiation and a sensor, such as a camera, CCD (Charge Coupled Device) sensor, photodiode, or similar, that senses the sample radiation. The enclosure typically includes a window to allow illuminating radiation and sample radiation to pass therethrough, whilst protecting internal components, such as the radiation source and sensor. A cover is moveably mounted to the enclosure, to allow the cover to move between an open position in which the window is exposed and a closed position in which the window is covered.

The above described spectrometer arrangement is particularly beneficial as this enables a sample to be easily provided for analysis whilst the spectrometer components and in particular radiation source and sensor are protected from the environment. Additionally, providing a cover which is naturally biased into a closed position ensures that the window through which illuminating, and sample radiation passes is protected from the environment, reducing the chances of this becoming damaged or exposed to contaminants, such as dust, which in turn can affect readings.

It will be appreciated that the above described spectrometer can have other applications, particularly in respect of capturing spectral data in an agricultural environment, and that reference to use of this in the above described agricultural condition determination process is not intended to be limiting.

A number of further features of the spectrometer will now be described.

In one example, the cover can be substantially parallel to the window, substantially perpendicularly to the radiation source and/or substantially perpendicularly to the sensor, and in one example, is configured to move in a direction substantially perpendicular to the window. This can help ensure the sample is urged into engagement with the window, and that the cover is aligned with the housing so that light is unable to enter the region between the cover and the window. In one example, this can avoid problems associated with stressing of hinge based arrangements, as may occur for example in attempting to achieve sealing engagement whilst accommodating thicker samples.

In one example, a biasing mechanism is provided, which biases the covering to the closed position, whilst an actuator is provided that can be used to urge the cover into an open position. However, this is not essential, and alternatively the cover can be held in place manually, for example, by having a user hold the cover in place, although more typically biasing mechanisms can be used so that the lid is biased into a closed position by default.

In one example, the enclosure and/or cover can include a deformable material, such as a rubberised foam, rubber or other polymeric material, extending around an extent of the window, to further reduce ingress of ambient radiation and/or contaminants, particularly when a sample is provided between the cover and window. This assists in protecting the equipment, and avoiding contamination by dust and ambient radiation, which could adversely affect measured spectra.

The cover can also include an optical surface, such as a reflective surface, to maximise reflection of radiation, so that as much radiation as possible is returned to the sensor, thereby improving signal to noise characteristics. In one example, the optical surface includes a fluoropolymer, such as spectralon, although other suitable materials could be used.

The optical surface could also be used to provide calibration, for example by having a set known frequency response, so that this can be used to calibrate the sample radiation against known wavelengths, which can assist in reducing the impact of sensor drift and other measurement inaccuracies. The cover can also include an optical surface window, such as a sapphire window, that protects the optical surface, preventing damage and contamination.

In one example, the optical surface is typically orientated substantially parallel to the window, so that the optical surface is substantially perpendicularly to the radiation source and/or the sensor, which can help ensure consistent reflection of radiation from the optical surface to the sensor. This in turn helps ensure the radiation emitted from the optical surface is detected consistently by the sensor over multiple measurements, which in turn allows this to act as a consistent reference, allowing measurements of sample radiation to be interpreted more accurately.

In one example, the cover includes a sample biasing mechanism configured to urge the sample towards the window. In one particular example, the cover can include an outer cover configured to substantially surround the window and a spring mounted inner cover supporting an optical surface, wherein the inner cover is configured to urge the sample against the window. This arrangement helps ensure consistent reflection of the optical surface, whilst biasing the sample against the window, whilst preventing light ingress, which can adversely affect readings.

The housing can also include a handle configured to allow hand-held operation of the spectrometer, with an optional mounting being provided to allow the client device to be coupled to the housing. This allows the spectrometer and client device to be held in one hand, allowing the user to manipulate a sample with the other hand, thereby facilitating the sample measurement procedure.

Whilst the above described techniques can be applied to a wide variety of samples, particular examples include any one or more of plant material, grain material, soil material, or the like. Particular examples include wheat, barley, canola, oats, rice, sorghum, grasses, fruits, lupins, pulses, beans, peas, or the like.

Figure 2:
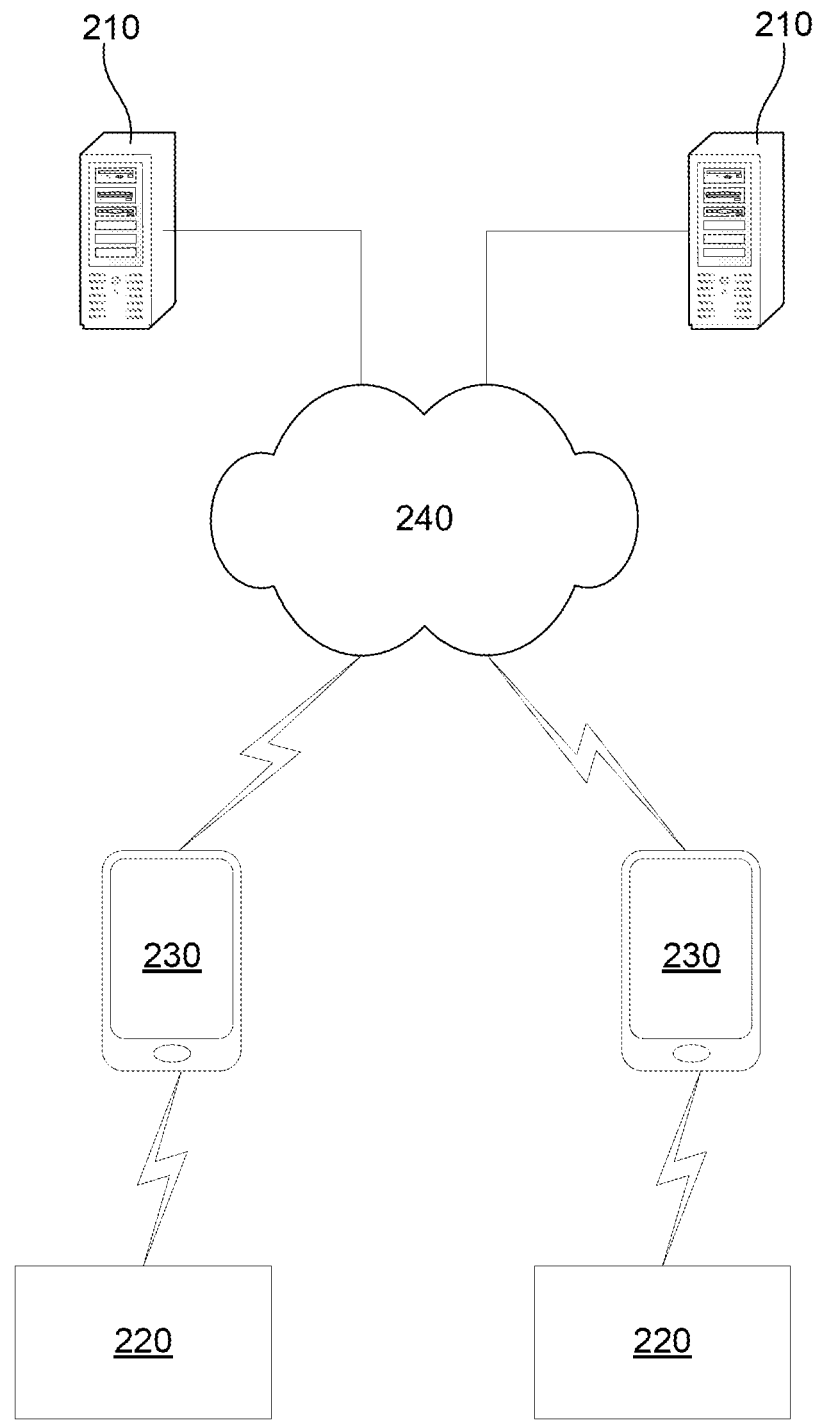
FIG. 2 is a schematic diagram of an example of a system for determining an agricultural condition in an agricultural environment.

An example of a system for determining an agricultural condition in an agricultural environment will now be described with reference to FIG. 2.

In this example, the system includes one or more processing systems 210 connected to one or more client devices 230 via communications networks 240, such as the Internet, and/or a number of local area networks (LANs). The client devices 230 are also connected to respective spectrometers 220, typically using a short-range communication protocol, or the like, to allow spectral data to be acquired and transferred to the processing devices 210 for analysis.

It will be appreciated that the configuration of the networks are for the purpose of example only, and in practice the processing systems 210 and client devices 230 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like. Furthermore, whilst the processing systems 210 are shown as single entities, it will be appreciated that the processing systems 210 can be distributed over a number of geographically separate locations, for example as part of a cloud-based environment. However, the above described arrangement is not essential and other suitable configurations could be used.

Figure 3:
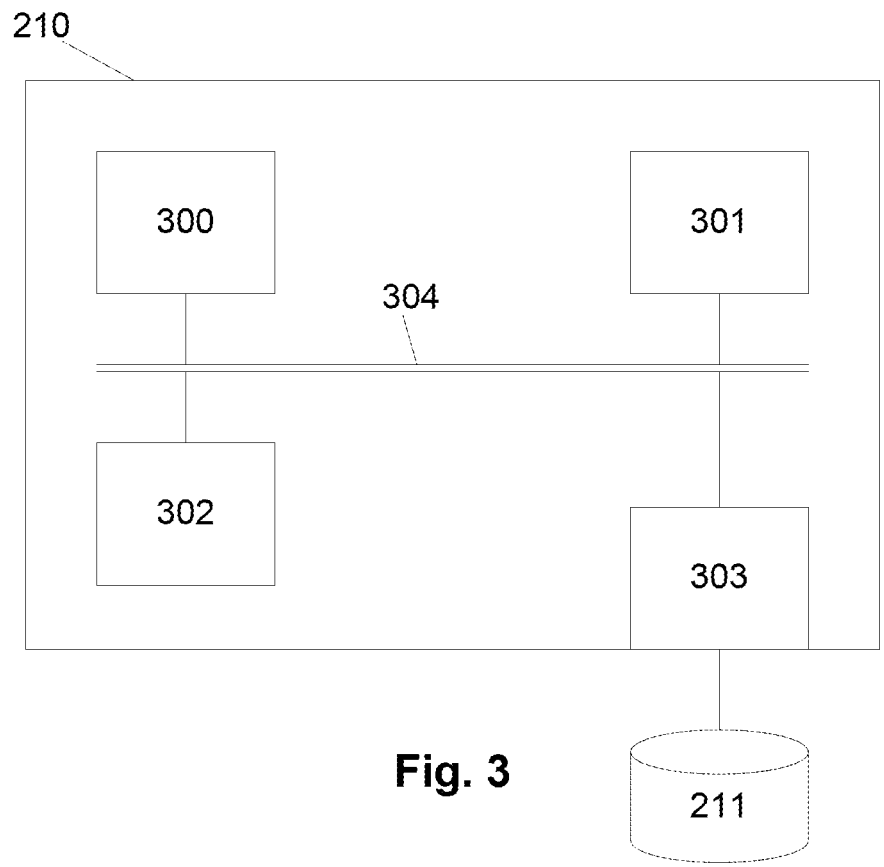
FIG. 3 is a schematic diagram of an example of a processing system.

An example of a suitable processing system 210 is shown in FIG. 3. In this example, the processing system 210 includes at least one microprocessor 300, a memory 301, an optional input/output device 302, such as a keyboard and/or display, and an external interface 303, interconnected via a bus 304 as shown. In this example the external interface 303 can be utilised for connecting the processing system 210 to peripheral devices, such as the communications networks 240, databases, other storage devices, or the like. Although a single external interface 303 is shown, this is for the purpose of example only, and in practice multiple interfaces using various methods (e.g. Ethernet, serial, USB, wireless or the like) may be provided.

In use, the microprocessor 300 executes instructions in the form of applications software stored in the memory 301 to allow the required processes to be performed. The applications software may include one or more software modules, and may be executed in a suitable execution environment, such as an operating system environment, or the like.

Accordingly, it will be appreciated that the processing system 210 may be formed from any suitable processing system, such as a suitably programmed client device, PC, web server, network server, or the like. In one particular example, the processing system 210 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 4:
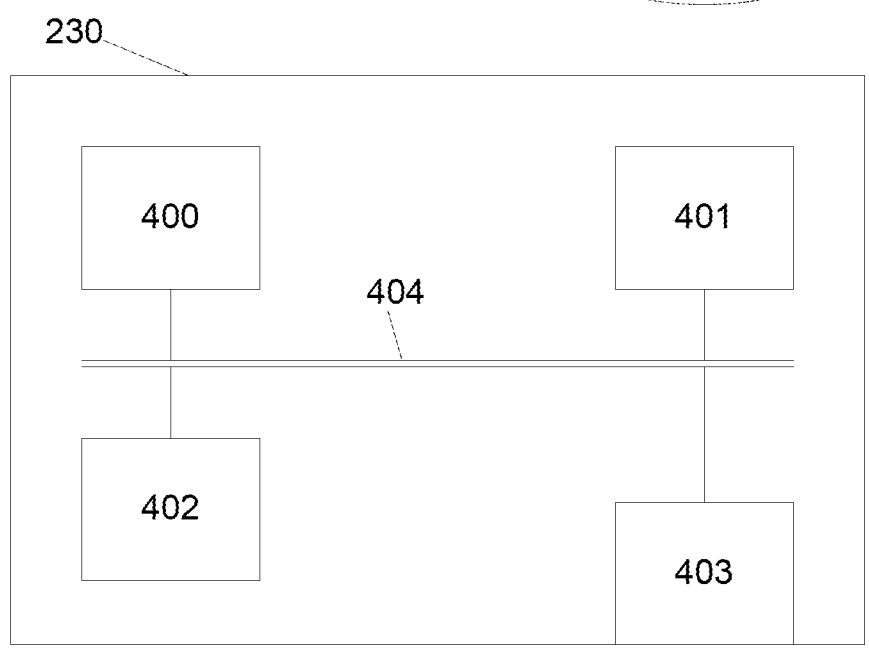
FIG. 4 is a schematic diagram of an example of a client device.

As shown in FIG. 4, in one example, the client device 230 includes at least one microprocessor 400, a memory 401, an input/output device 402, such as a keyboard and/or display, and an external interface 403, interconnected via a bus 404 as shown. In this example the external interface 403 can be utilised for connecting the client device 230 to peripheral devices, such as the spectrometers 220, the communications networks 240, databases, other storage devices, or the like. Although a single external interface 403 is shown, this is for the purpose of example only, and in practice multiple interfaces using various methods (e.g. Ethernet, serial, USB, wireless or the like) may be provided.

In use, the microprocessor 400 executes instructions in the form of applications software stored in the memory 401 to allow for communication with the spectrometers 220, the processing devices 210, as well as to allow user interaction for example through a suitable user interface.

Accordingly, it will be appreciated that the client devices 230 may be formed from any suitable processing system, such as a suitably programmed PC, Internet terminal, laptop, or hand-held PC, and in one preferred example is either a tablet, or smartphone, or the like. Thus, in one example, the processing system 210 is a standard processing system such as an Intel Architecture based processing system, which executes software applications stored on non-volatile (e.g., hard disk) storage, although this is not essential. However, it will also be understood that the client devices 230 can be any electronic processing device such as a microprocessor, microchip processor, logic gate configuration, firmware optionally associated with implementing logic such as an FPGA (Field Programmable Gate Array), or any other electronic device, system or arrangement.

For the purpose of the following examples, it is assumed that one or more processing systems 210 are servers, which communicate with the client device 230 via a communications network, or the like, depending on the particular network infrastructure available. The servers 210 typically execute applications software for performing required tasks including storing, searching and processing of data, with actions performed by the processing system 210 being performed by the processor 300 in accordance with instructions stored as applications software in the memory 301 and/or input commands received from a user via the I/O device 302, or commands received from the client device 230.

It will also be assumed that the user interacts with the server 210 via a GUI (Graphical User Interface), or the like presented on the client device 230, and in one particular example via a browser application that displays webpages hosted by the server 210, or an App that displays data supplied by the processing system 210. Actions performed by the client device 230 are performed by the processor 400 in accordance with instructions stored as applications software in the memory 401 and/or input commands received from a user via the I/O device 402.

However, it will be appreciated that the above described configuration assumed for the purpose of the following examples is not essential, and numerous other configurations may be used. It will also be appreciated that the partitioning of functionality between the client devices 230, and the processing systems 210 may vary, depending on the particular implementation.

Figure 5A:
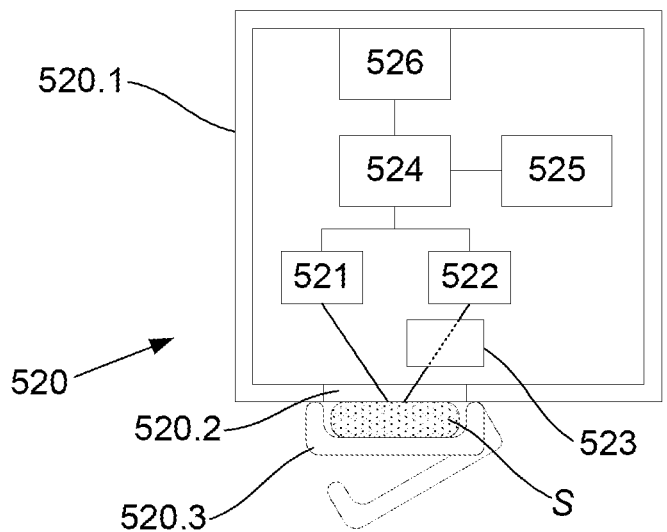
FIG. 5A is a schematic diagram of an example of a spectrometer.

An example spectrometer will now be described in more detail with reference to FIGS. 5A and 5B.

In this example, the spectrometer 520 includes a housing 520.1 having a window 520.2 therein. A cover 520.3 is provided which is typically hingeably mounted to the enclosure 520.1, allowing this to be moved between the closed position shown in FIG. 5A and an open position shown in dotted lines. This allows a sample to be provided in abutment with the window 520.2 and enclosed by the cover 520.3 when a reading is performed.

Figure 5B:
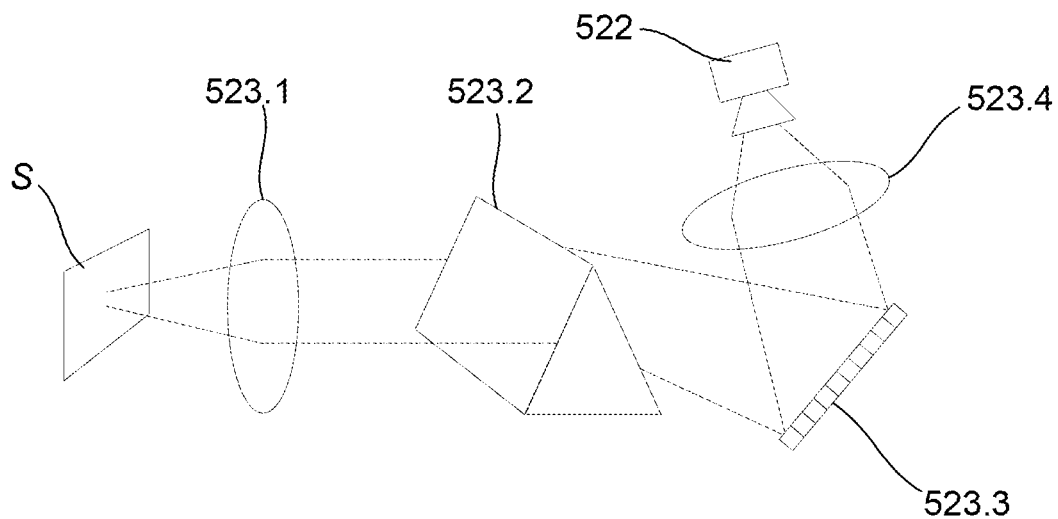
FIG. 5B is a schematic diagram of an example of an optical system of the spectrometer of FIG. 5A.

Internally the spectrometer includes a radiation source 521, such as a lamp and a sensor 522, such as a photodiode, which detects radiation received via an optical system 523, an example of which is shown in further detail in FIG. 5B.

In this example, the optical system 523 includes input optics 523.1 that receive sample radiation. The input optics can be any suitable form of optical arrangement capable of capturing electromagnetic radiation emitted or reflected from the sample, and this can include one or more imaging lenses, an aperture, or the like. The input optics 523.1 focus radiation on a spectral modulator 523.2, such as a prism, diffraction grating, or the like, which spatially disperses different spectral bands of radiation. The dispersed radiation is then selectively transferred to output optics 523.4 and the sensor 522, using a controlling device 523.3, such as digital mirror device (DMD), Liquid Crystal on Silicon (LCOS) device, or the like. This allows the spectrometer to selectively direct spatially separated radiation to the sensor, so that the intensity of radiation at different wavelengths can be measured by the sensor independently. It will be appreciated however, that different configurations could be used depending on the preferred implementation.

The spectrometer further includes a spectrometer processor 524, spectrometer memory 525 and an external interface 526. In use, operation of the spectrometer is controlled by the spectrometer processor 524, which operates in accordance with instructions stored in the spectrometer memory 525. Specifically, the spectrometer processor controls the radiation source 521, sensor 522 and control device 523.3, to thereby expose the sample and then measure the intensity of the reflected/transmitted radiation at different wavelengths. The processor 524 operates to receive signals from the sensor 522 and optionally at least partially process these to generate spectral data. It will be appreciated as part of this the system can digitise and optionally filter the measured signals, performing other processing as required to thereby generate the spectral data, which can then be output via the interface 526, allowing this to be transferred to the client device 230 typically using a short-range communications protocol such as Bluetooth or the like.

In one example, the spectrometer is configured to operate over a wavelength range of 900 nm to 1700 nm, although it will be appreciated that this is not intended to be limiting and other wavelength ranges could be used.

Figure 6A:
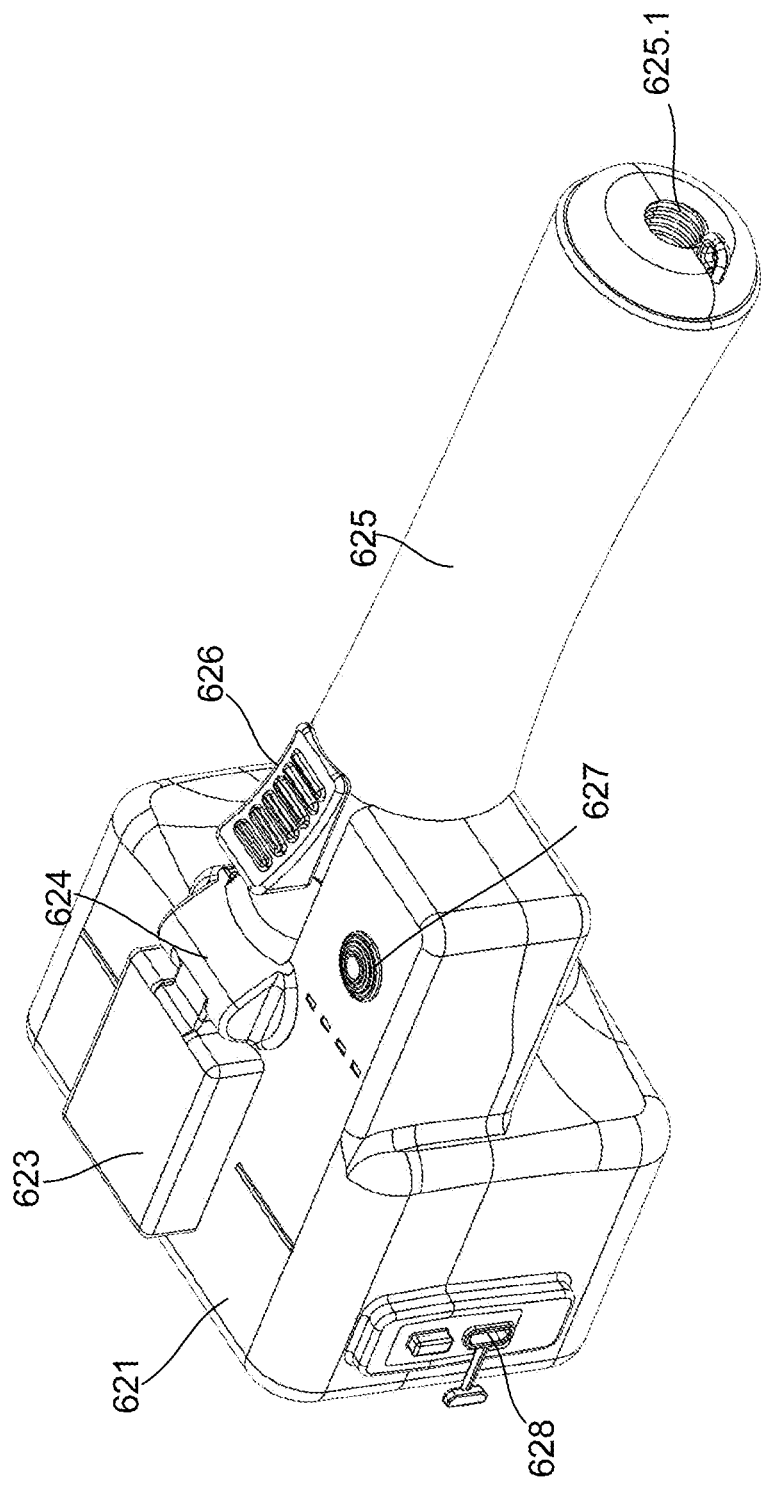
FIG. 6A is a schematic perspective view of an example of a spectrometer housing.
Figure 6B:
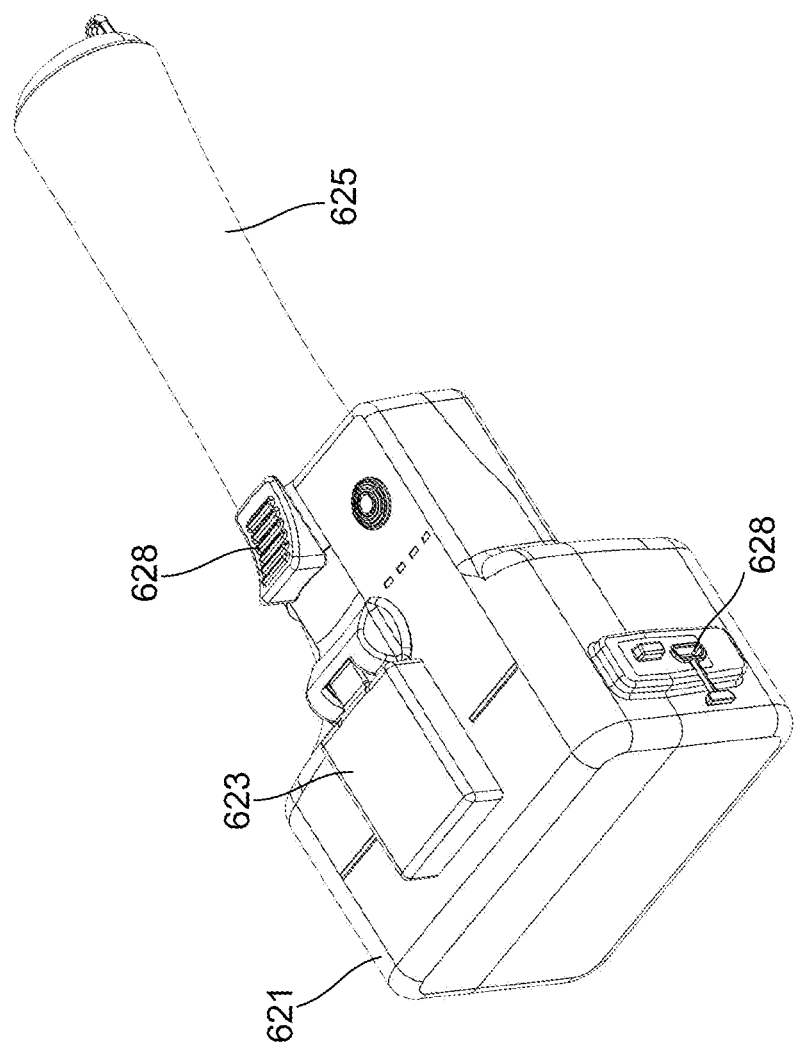
FIG. 6B is a schematic topside perspective view of the spectrometer housing of FIG. 6A.
Figure 6C:
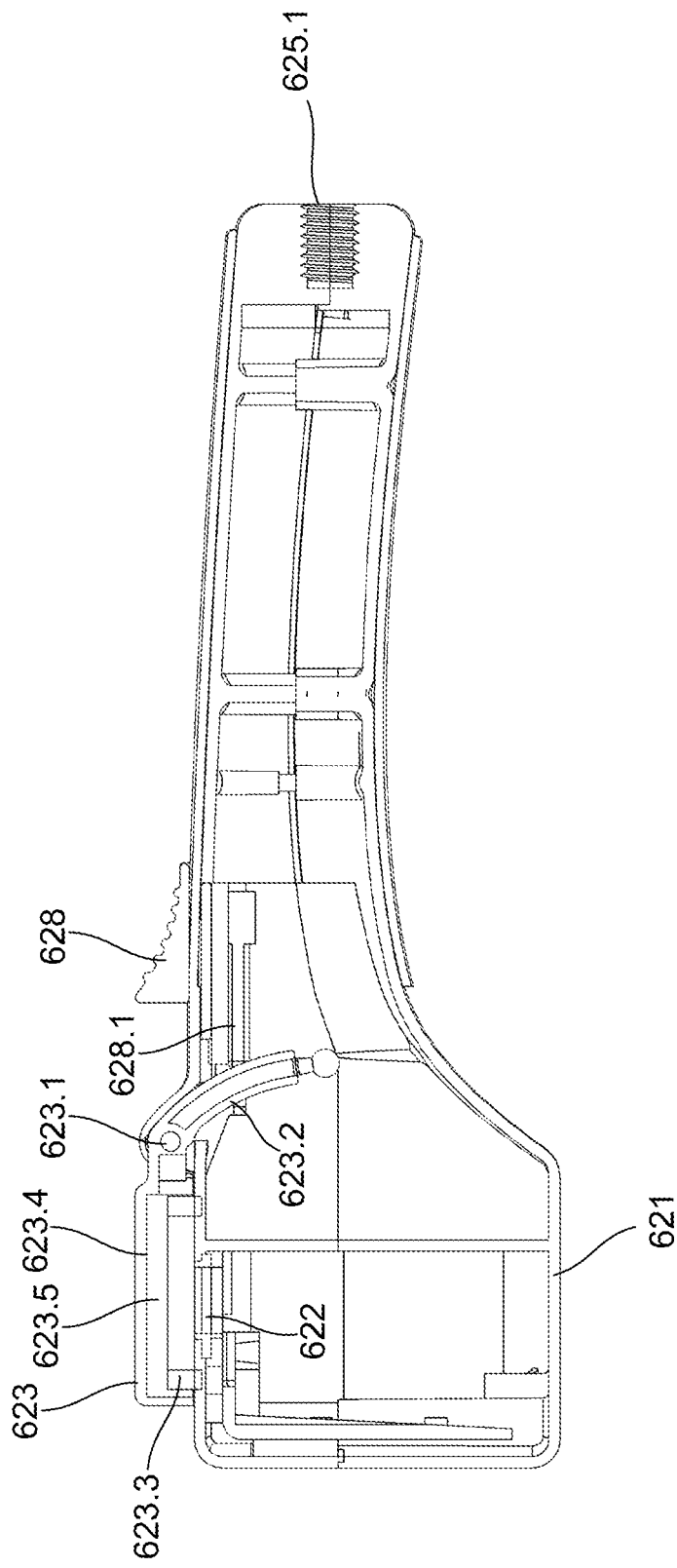
FIG. 6C is a schematic side cutaway view of the spectrometer housing of FIG. 6A.

A specific preferred example of the physical configuration of the housing is shown in more detail in FIGS. 6A to 6C.

In this example, the housing includes an enclosure 621, defining an internal cavity that houses the spectrometer components described above. The enclosure includes a window 622, which in use is aligned with the sensor 522 and radiation source 521, allowing illuminating and sample radiation to pass therethrough.

A handle 625 projects outwardly from the enclosure 621, with an opposing end of the handle including a screw fitting 625.1, which can be used to connect the handle to a mounting (not shown), which in use can support the client device 230. This enables the spectrometer and client device to be held via a common handle, enabling singlehanded operation of the spectrometer and client device, which can assist with managing sample collection and measurement in the field.

A cover 623 is attached to a curved arm 623.2 that extends into the housing, with the cover and arm being attached to a pivotal mounting 623.1, thereby hingeably mounting the cover 623 to the enclosure. In one example, the pivotal mounting 623.1 includes a torsion spring (not shown) to bias the cover 623 into the closed position shown. An actuator in the form of a thumb slider 628 is mounted on the handle 625, with the slider 628 including a finger 628.1 provided within the handle 625, which can be urged into engagement with the curved arm 623.2, when the user applies a longitudinal pressure to the slider 628. As a result, movement of the slider 628 biases the arm 623.2, and hinges the cover into an open position. The slider 628 is also typically spring loaded, returning to its original position to thereby release the cover 623, when the operator ceases applying pressure. This enables an operator to open the cover 623 by using their thumb to push the slider 628 along the handle 625 towards the enclosure 621, position the sample, and release the slider 628 to thereby sandwich the sample between the window and cover, allowing this to be performed singlehandedly, while holding the handle 625. The cover may also be optionally removable for example to allow alternative samples to be analysed.

The cover 623 includes an internal underside optical surface 623.4, protected by a sapphire window 623.5. A foam surround 623.3 is provided mounted to the enclosure 621 around the window, so as to surround the window 622 in use, to thereby prevent ambient light entering into the spectrometer and thereby effecting readings in use. These features, in combination, help ensure that samples are exposed to consistent radiation each time a measurement is performed, and that maximum sample radiation is returned to the sensor, thereby increasing the accuracy and repeatability of the measurements performed.

An optional input button 627 can be provided, for example to turn the spectrometer on and off, whilst an external interface 628, such as a USB port can be provided, to allow the spectrometer to be connected to a computer.

Figure 7A:
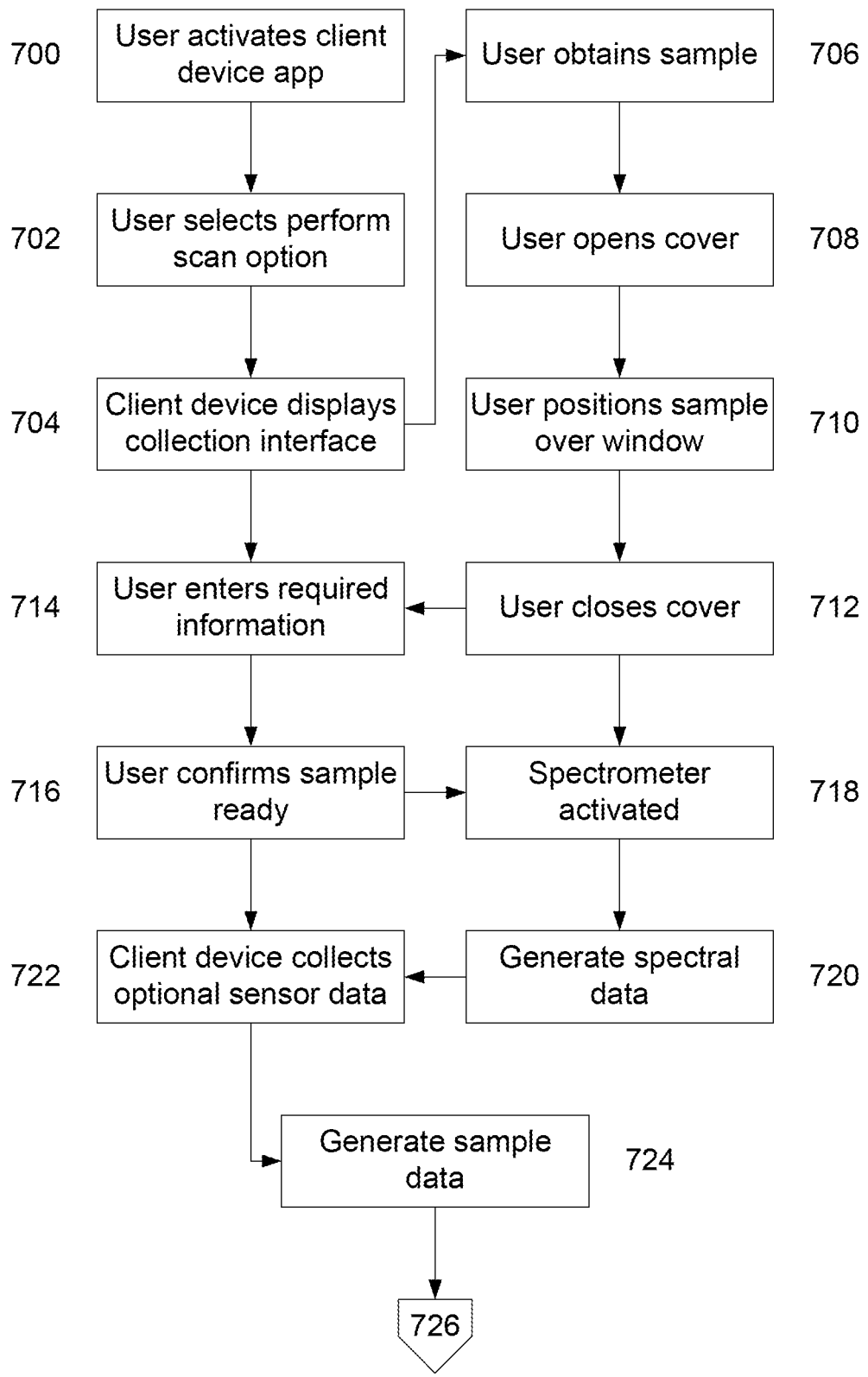
FIGS. 7A to 7C are a flowchart of a specific example of a process for determining an agricultural condition in an agricultural environment; and, FIG. 8 is a flowchart of an example of a process for generating a computational model; and, FIG. 9A is a schematic diagram of a further example of a spectrometer with the cover in an open position; and, FIG. 9B is a schematic diagram of the spectrometer of FIG. 9A with the cover in a closed position.
Figure 7B:
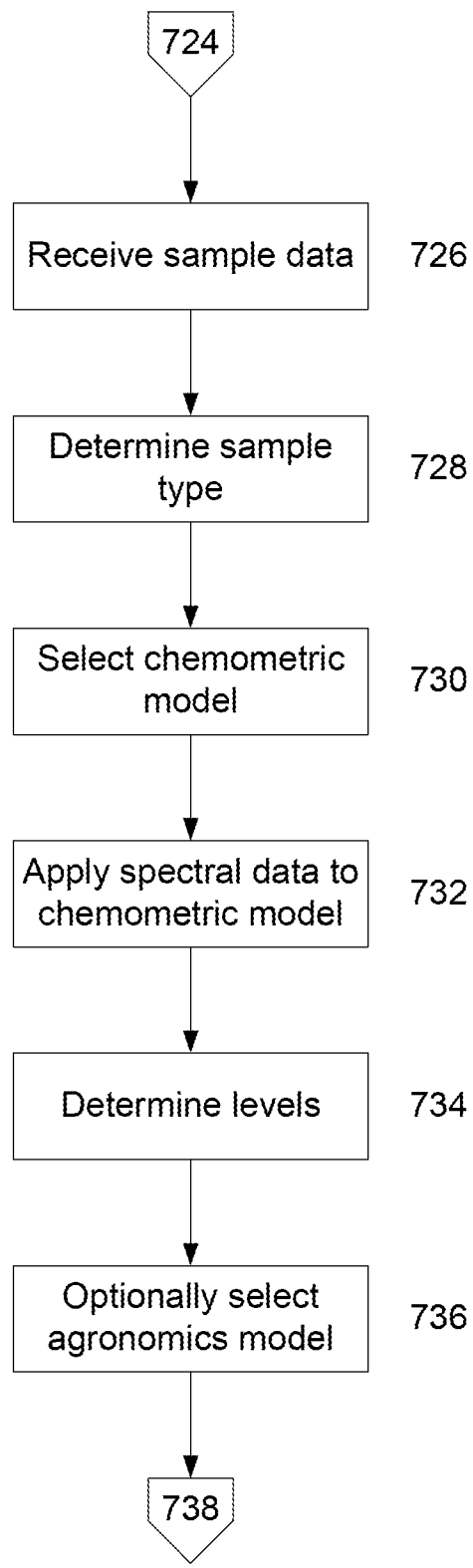
Figure 7C:
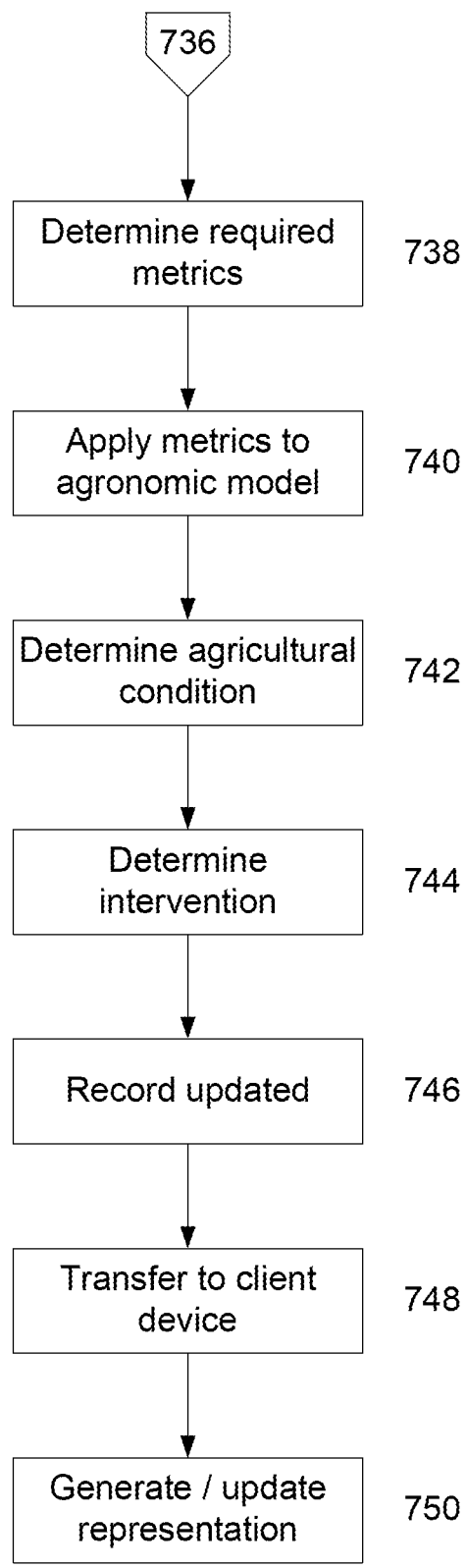

An example of the process for performing a nutrient assessment will now be described with reference to FIGS. 7A to 7C.

In this example, at step 700 a user activates a client device app on the client device 230. The user then typically selects a 'Perform Scan' option presented via a user interface at step 702, which causes the client device 230 to display a collection interface at step 704. The collection interface is used to control the data collection process, and can include fields defining information to be input by the user, and optionally showing a series of instructions guiding the user through the sample scanning process.

To perform sample measurements, at step 706 the user obtains the sample and opens the cover 623, using the thumb slider 628, at step 708. The user positions the sample S in abutment with the window 622 at step 710, before releasing the thumb slider 628, allowing the cover 623 to close at step 712, thereby sandwiching the sample between the window 622 and cover 623.

Simultaneously and/or sequentially with this process, at step 714 the user enters any required information, such as one or more of the sample or environmental parameters described above, via the data collection interface. Specifically, the interface will prompt the user to provide information such as an indication of the sample type, or the like.

It will be appreciated that as part of the above process, the collection interface may be pre-populated with any available data, for example information may be retrieved from a remote database. For example, if the user has previously measured samples at the same physical location within the agricultural environment, at least some required information, such details of a crop history, details of prior treatments, a crop type, or the like, could be retrieved from previous records and used to populate the fields, reducing the amount of user input required.

Other remote data sources could also be used to populate these fields or add further details. This could include predictions of growth stage and crop density derived from analysis of spectral data in optical, infra-red or radar wavelengths captured by a remote sensing platform such as satellites, manned or un-manned aerial vehicles, or localised predictions derived from models using equations and/or multiple geo-spatial datasets gathered from different sensor types at multiple temporal (time) and spatial (space) resolutions. Such automated population could occur at any stage of the process, and could occur when the interface is initially displayed to the user at step 704 above, depending on the preferred implementation.

As part of this process, at step 716 the user can select an appropriate input option confirming that the sample is ready for the measurement procedure to be performed, thereby causing the client device 230 to activate the spectrometer 220 at step 718. In particular, the client device 230 generates instructions, which cause the spectrometer processor 524 to activate the lamp 521, control the DMD 523.3 and measure radiation that is received via the sensor 522. The spectrometer processor 524 generates spectral data at step 720, forwarding this to the client device 230, via the spectrometer external interface 526.

At step 722 the client device 230 collects optional sensor data from one or more sensors, potentially including rainfall data from a rainfall sensor, temperature data from a temperature sensor, humidity data from a humidity sensor, wind data from a wind sensor, or the like. At step 724 the client device generates sample data which is indicative of the spectral data, together with any other provided information, such as one or more sample or environmental parameters, sensor data, or the like.

At step 726 the sample data is transferred to the server 210, which operates to determine a sample type and/or variety from the input sample information at step 728. The server 210 uses the determined sample type to select a corresponding chemometric model at step 730, which is specific to that sample type. The spectral data is then applied to the chemometric model at step 732, typically by deriving metrics in the form of the intensity of the sample radiation at different wavelengths. Thus, this could be used to identify the intensity at wavelengths corresponding to absorption by particular nutrients, such as nitrogen or the like. These spectral metrics are then applied to the chemometric model, with the output being indicative of levels of one or more nutrients or other sample constituents at step 734.

If one or more agronomic models are available, one of these is selected at step 736, with required metrics being determined by the server 210 at step 738. For example, the agronomic model may require different inputs, depending on the analysis that is to be performed, such as details of nutrient levels in the sample, as well as one or more sample or environment parameters. Accordingly, the one or more required metrics are determined from the sample data and/or retrieved from other sources. For example, this can include retrieving previous measurements for the agricultural environment from one or more records, retrieving data, such as a biomass or other measurements from a GIS, retrieving climate data, such as previous and forecast rainfall, from a metrological database or similar. Once the metrics have been determined, these can be applied to the agronomic model at step 740.

At step 742 the results of the analysis provide an agricultural condition indicator which is indicative of the current agricultural condition of either the sample and/or the agricultural environment. As part of this, the agricultural condition could be indicative of a nutrient status, and may therefore show relative levels of different nutrients, but could also be applied to other plant health indicators like water content or the levels of phytohormones such as abscisic acid (ABA), salicylic acid (SA), jasmonic acid (JA) and ethylene, or the like. As opposed to simply indicating levels of particular nutrients however, the agricultural condition is typically additionally and/or alternatively interpretative, and can be indicative of the expected productivity, yield and/or plant health that will result from the particular sample constituents. For example, the results of the analysis could predict there is only a 60% chance of achieving target yield, or might indicate that levels of particular major nutrients require correction to improve plant health.

Additionally, at step 744, the agricultural condition could be used together with a suitable model to determine one or more recommendations for enhancing the agricultural condition of the environment. In this regard, the model can output the predicted nutrient levels, with this information then being compared to ideal nutrient levels for the environment, given the current environment usage, with recommendations being provided based on knowledge of available nutrient supplement products, such as particular fertilisers, or other available actions. As previously indicated, this can take into account information regarding target yields, as well as economic factors, such as the current crop and fertiliser prices, in order to provide recommendations to maximise revenue.

At step 746 an agricultural environment record is updated. In one example, this is performed to allow the system to be utilised to perform longitudinal monitoring in which changes in agricultural condition are tracked. This can be performed for the purpose of monitoring changes in agricultural condition, including assessing the efficacy of a treatment regimen or program, such as the application of particular fertilisers. As part of this process, a comparison can be performed between a current and previous agricultural condition, with results of the comparison being used to track treatment effectiveness.

At step 748 an indication of an agricultural condition and/or recommendations can be transferred to the client device 230, allowing a representation of the agricultural condition to be generated and displayed at step 750. The nature of the representation will vary depending on the preferred implementation and in one example, could include a simple indicator indicative of whether the agricultural environment has a good, bad or indifferent agricultural condition, either collectively, or for different individual nutrients separately. Alternatively, this could be indicative of particular levels of specific nutrients, for example specifying a particular concentration, optionally showing this compared to an idealised value, allowing the user to rapidly understand potential nutrient deficiencies.

Additionally, the representation could include a recommendation of nutrient supplements which should be used, or other actions that can performed. For example, this could recommend the application of a particular fertiliser in combination with a particular irrigation program, or suggest improved sample collection processes, such as suggesting locations where further sample collection might be beneficial. In addition to simply providing a recommendation, the representation would typically include information regarding the expected implications of the recommendations, including expected changes in yield and revenue, allowing the farmer to make informed decisions regarding the interventions to be implemented.

In one preferred example, the representation is provided as part of a geographic information system (GIS), with a map being used to show the agricultural environment, together with locations from which samples were collected. This can be overlaid with information regarding the agricultural condition, and any recommended actions, with additional GIS layers optionally being used to show additional information, such as climate information or the like. The map could highlight areas where additional sampling is required, for example by identifying areas of low historical yield from previous measurements, or low current yield derived from biomass measurements performed by remote sensing, guiding the farmers in ongoing monitoring on the ground. Additionally, the map can show highly localised interventions, specifically the process can be used to determine Variable Rate Application (VRA) interventions, that prescribe precise rates of nutritional or soil amendments for different areas, or the like.

This allows a user to view relevant information via a map-based interface, allowing them to more rapidly evaluate the areas of the environment in which action is required, and can help understand how different areas of a property might require different actions. Additionally, by integrating the output into a GIS this allows the information to be used in controlling implementation of the interventions. For example, the GIS can be used to generate prescription files, which are in a machine-readable GIS file format that prescribes precise rates for implementing VRA at different areas within a field. In practice this could drive in field machinery or robots to allow for the more precise application of treatments (e.g. nutrients, pest & disease control), providing focused treatments and/or variation of treatment rates throughout paddock zones, based upon specific zone needs.

The GIS system could be used to generate profit maps represented on a digital farm map derived from the GIS database, available both during and post the growing period, which would draw upon variables including target and actual yield data as well as prescribed nutrient application costs, aiding the grower to make their final application decisions.

Feedback reports could be provided post the season, which would highlight the efficacy of prescribed nutrition and treatment application recommendations in terms of yield and profit outcomes, providing machine learning opportunities for the invention's models i.e. opportunities to further refine the solution and prescriptions.

The system could be further used to provide visualised results from scanning activities on a digital farm map, from the GIS database, which further allows visual comparisons of scanning results across different growing seasons as well as intra-season comparisons.

Figure 8:
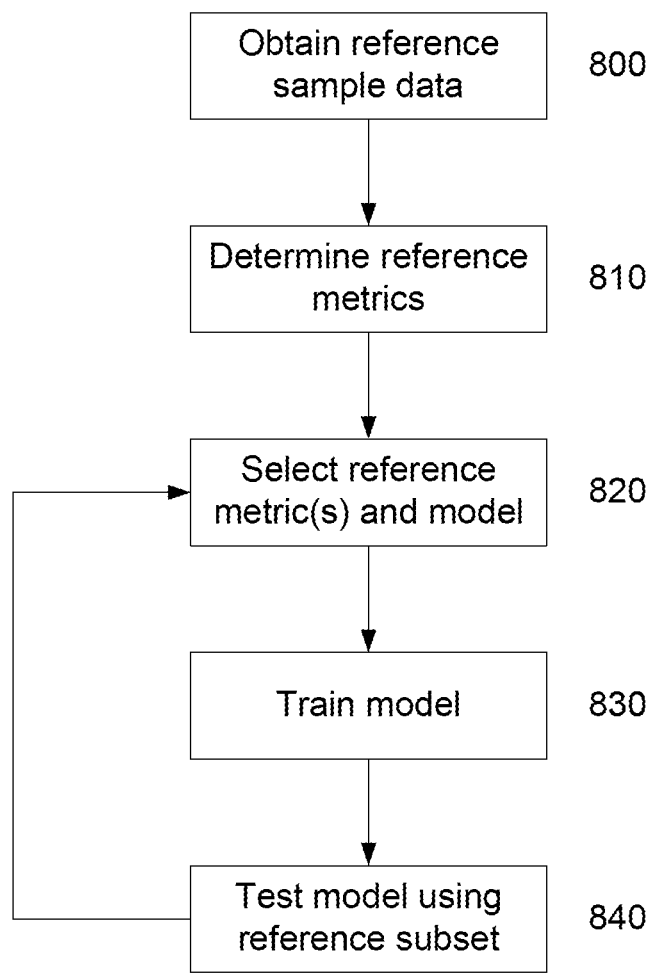

In the above described approaches, one or more computational models are used in order to determine an agricultural condition, and an example of a process for generating such model(s) will now be described with reference to FIG. 8.

In this example, reference sample data is obtained at step 800. The reference sample data includes spectral data, as well as other parameters, and can be collected using a process generally similar to that described above with respect to steps 700 to 726. At step 810 the reference sample data is analysed to determine one or more reference metrics, including sample and agricultural parameters, as well as spectral parameter metrics from the acquired spectral data. As part of this process, additional data would be collected to ascertain an agricultural condition in the agricultural environment, optionally using this to determine interventions, such as nutrient application rates that will achieve optimal yield outcomes. This could involve collecting additional samples, such as soil samples prior to seeding, and analysing these using traditional techniques, such as forwarding these to a laboratory.

Once the data is collected, the reference sample data is used in training a computational model. To achieve this, the reference sample data is typically used to determine all possible metrics that could be used by the computational model, allowing this to be used in order to ascertain which of the metrics are most useful in discriminating between different growing conditions.

At step 820 a combination of the reference metrics and one or more generic computational models are selected, with the reference metrics and identified agricultural condition and/or measured nutrient levels, being used to train the model at step 830. The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail.

In addition to simply generating the model, the process typically includes testing the model at step 740 to assess the performance of the trained model. Such testing is typically performed using a subset of the reference sample data, and in particular, different reference sample data to that used to train the model, to avoid model bias. The testing is used to ensure the computational model provides sufficient discriminatory performance. In this regard, the discriminatory performance is typically based on an accuracy, sensitivity, specificity and AUROC, with a discriminatory performance of at least 70% being required in order for the model to be used.

It will be appreciated that if the model meets the discriminatory performance, it can then be used in determining an agricultural condition using the process outlined above with respect to FIG. 1. Otherwise, the process returns to step 730 allowing different metrics and/or models to be selected, with training and testing then being repeated as required until the required discriminatory ability is obtained.

Thus, in one example, the one or more processing devices select a plurality of reference metrics, typically selected as a subset of each of the metrics listed above, train one or more computational models using the plurality of reference metrics, test the computational models to determine a discriminatory performance of the model(s) and if the discriminatory performance of the model(s) falls below a threshold then selectively retrain the computational model(s) using a different plurality of reference metrics and/or train different computational model(s). Accordingly, it will be appreciated that the above described process can be performed iteratively utilising different metrics and/or different computational models until a required degree of discriminatory power is obtained.

As an alternative, the one or more processing devices can select a plurality of combinations of reference metrics, train a plurality of computational models using each of the combinations, test each computational model to determine a discriminatory performance of the model and select the computational model with the highest discriminatory performance for use in determining an agricultural condition.

In addition to using the metrics to train the models, the training can also be performed taking into account different sample and/or agricultural parameters, so that models are specific to particular sample types and/or varieties, and/or different agricultural environments. In one example, this process involves having the one or more processing devices perform clustering to determine clusters of similar samples, for example using a clustering technique such as k-means clustering, and then training the computational model at least in part using the clusters. For example, clusters of samples of a similar type can be developed, with these being used to derive models specific for that type of sample. Thus, this results in a suite of chemometric and agronomic models, with different models being applicable to different scenarios, such as different sample types. It will also be appreciated that models could be derived on a per user basis, for example customising models for users so that they are specific to the particular requirements of the user and the respective agricultural environment, thereby providing a more personalised output.

In a further example, the processing devices develop the model by performing one or more of feature analysis and downselection, correlation and univariate statistical separability tests and dimensionality reduction. Thus, for example, this allows for the calculation of multiple metrics, and multiple models, with those refined depending on their discriminatory power. Such refining can be performed using one or more of cross-validation performance, hyperparameter validation, learning curve analysis or metric relevance across models.

Accordingly, the above described techniques provide a mechanism for training one or more computational models to determine an agricultural condition and/or provide a nutrient recommendation. It will be appreciated that the process can be used to develop both chemometric and agronomic models.

Figure 9A:
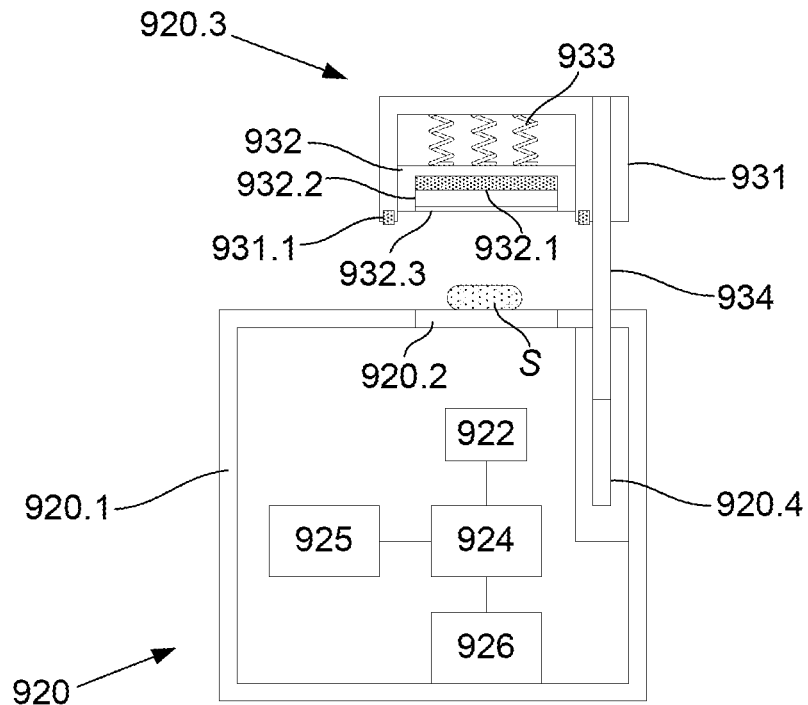
Figure 9B:
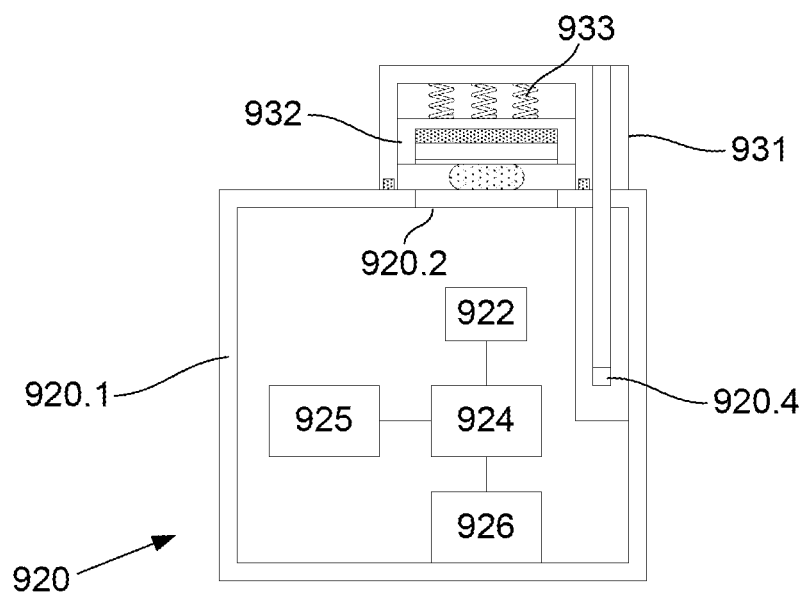

A further example of an apparatus including a spectrometer incorporated into a customised housing will now be described in more detail with reference to FIGS. 9A and 9B.

In this example, the apparatus 920 includes a housing 920.1 having a scanning window 920.2 therein, and a cover 920.3. Internally the apparatus includes a spectrometer includes a radiation source (not shown), such as a lamp and a sensor 922, such as a photodiode, which detects radiation received via an optical system (not shown). The spectrometer further includes a spectrometer processor 924, spectrometer memory 925 and an external interface 926. It will be appreciated that operation of the spectrometer is therefore broadly similar to the example described above with respect to FIGS. 5A and 5B, and this will not therefore be described in any further detail.

In this example, the cover 920.3 is configured to move perpendicularly to the housing and hence window. Specifically, the cover 920.3 includes an outer cover 931, which in this example is a rectangular cuboid with an open underside, which is configured to sit over the sample and window. A shaft 934 extends from the outer cover 931 and is slidably mounted within a channel 920.4 in the housing 920.1, allowing the outer cover 931 to be raised as shown in FIG. 9A, to enable a sample S to be positioned on the window 920.2, and lowered as shown in FIG. 9B, to thereby enclose the sample S and window 920.2.

A seal 931.1 is provided around a perimeter of an underside of the outer cover 931, so that this is compressed against the housing 920.1, thereby sealing the internal space within the outer cover 931, and thereby preventing ingress of external illumination. The seal could be formed from foam, but is more typically a more resiliently deformable material, such as a rubber, or other polymeric material, or similar.

Additionally, the cover 920.3 includes an inner cover 932, which is mounted to an underside of the internal cavity of the outer cover 931 via springs 933, so that inner cover 932 can be biased in a downward direction, thereby helping urge the sample S against the window 920.2. In this example, the inner cover 932 includes a optical surface in the form of spectralon layer 932.2, which is mounted on a foam layer 932.1 mounted to an underside of the inner cover 932, and which has an outer protective sapphire glass layer 932.3. This arrangement, allows the spectralon layer 932.2 and sapphire glass layer 932.3 to be urged into engagement with the sample S.

It will be appreciated however that the dual cover arrangement is not required and that single cover arrangements could be used. It will also be appreciated that the cover arrangement could be used in conjunction with a range of different casing deigns, and that the examples provided herein are not intended to be limiting.

This arrangement can provide a number of benefits. Firstly, linear movement of the cover 920.3 avoids stressing of a hinge, which can result from accommodating thick samples under a hinged cover, whilst helping ensure adequate sealing around the sample to prevent ingress of ambient illumination. Additionally, this arrangement biases the spectralon layer 932.2 against the sample 5, so that the spectralon layer 932.2 remains perpendicular to the sensor 922 of the spectrometer, which in turn helps ensure consistent sensing of radiation emitted from the spectralon layer 932.2 in conjunction with sensing of radiation emitted from the sample S. This allows the radiation emitted from the spectralon layer 932.2 to be used as a consistent reference, in turn allowing sample radiation to be analysed more accurately.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. An apparatus for determining an agricultural condition in an agricultural environment, the apparatus including:
    a) one or more processing devices that:
        i) acquire spectral data by measuring sample radiation at least one of reflected from and transmitted through an agricultural sample obtained from the agricultural environment;
        ii) use the spectral data and at least one computational model to determine an agricultural condition, the computational model embodying relationships between the spectral data and different agricultural conditions by:
            (1) determining at least one metric associated with the agricultural environment by using the spectral data and a first computational model, the first computational model embodying relationships between the spectral date and the at least one metric, wherein the first computational model is a chemometric model; and
            (2) applying the at least one metric to the at least one computational model by using the at least one metric and a second computational model to determine the agricultural conditional, the second computational model embodying relationships between the at least one metric and the agricultural condition, wherein the second computational model is an agronomic model; and
        iii) use the agricultural condition to determine an indicator indicative of at least one of:
            (1) the agricultural condition; and
            (2) an intervention to improve the agricultural condition; and
    b) a spectrometer that exposes the agricultural sample to illuminating radiation and measures the sample radiation, the spectrometer including a housing having:
        i) an enclosure containing:
            (1) a radiation source that generates illuminating radiation; and
            (2) a sensor that senses sample radiation;
        ii) a window in the enclosure to allow illuminating radiation and sample radiation to pass therethrough;
        iii) a cover movably mounted to the enclosure to allow the cover to move between:
            (1) an open position in which the window is exposed; and
            (2) a closed position in which the window is covered, wherein in use a sample is provided between the cover and the window, allowing the measurement of sample radiation,
    wherein the at least one of the enclosure and the cover includes a deformable material extending at least part way around the window when the cover is in the closed position to thereby prevent ingress of at least one of ambient radiation and contaminants.

2. The apparatus according to claim 1, wherein the at least one computational model is derived at least one of:
    a) from reference spectral data measured for one or more reference agricultural samples from reference agricultural environments having known reference agricultural conditions; and
    b) from reference metrics associated with reference agricultural environments having known reference agricultural conditions; and,
    c) by applying machine learning to the reference spectral data.

3. The apparatus according to claim 1, wherein the one or more processing devices:
    determine the at least one metric using at least one of:
    a) at least one parameter; and,
    b) the spectral data, wherein the at least one metric relates to a constituent of the agricultural sample and the at least one metric corresponds to an intensity of sample radiation at one or more selected wavelengths.

4. The apparatus according to claim 3, wherein the at least one parameter at least one of:
    a) is determined by at least one of:
        i) using user input commands;
        ii) using sensor data received from one or more sensors;
        iii) retrieving the at least one parameter from a stored agricultural environment record;
        iv) retrieving the at least one parameter from a remote data store; and,
        v) retrieving the at least one parameter from a geographic information system (GIS); and,
    b) includes at least one of:
        i) a sample parameter including at least one of:
            (1) a sample type;
            (2) a sample variety;
            (3) a sample nutrient status;
            (4) a sample location;
            (5) a sample growth stage;
            (6) a sample growth history; and,
            (7) a sample target yield;
        ii) an agricultural environment parameter including at least one of:
            (1) an agricultural environment location;
            (2) intervention details;
            (3) a crop history;
            (4) a target yield or yield potential;
            (5) biomass development;
            (6) vegetation indices;
            (7) soil indices;
            (8) soil parameters including at least one of:
                (a) pH;
                (b) organic carbon levels;
                (c) particle size;
                (d) water holding capacity; and,
                (e) soil nutrient levels;
            (9) climate parameters including at least one of:
                (a) temperature;
                (b) rainfall;
                (c) humidity;
                (d) wind; and,
                (e) sunlight levels; and,
            (10) disease and pest incidences.

5. The apparatus according to claim 1, wherein the apparatus includes a client device in communication with the spectrometer and the one or more processing devices, wherein, in use:
  a) the spectrometer is used in the agricultural environment to:
    i) expose the agricultural sample to illuminating radiation;
    ii) measure the sample radiation; and,
    iii) generate spectral data indicative of the sample radiation; and,
  b) the client device:
    i) receives the spectral data from the spectrometer;
    ii) transfers at least the spectral data to the one or more processing devices;
    iii) receives the indicator from the one or more processing devices; and,
    iv) displays the indicator.

6. The apparatus according to claim 1, wherein the cover at least one of:
  a) is aligned at least one of:
    i) substantially parallel to the window;
    ii) substantially perpendicularly to the radiation source; and
    iii) substantially perpendicularly to the sensor;
  b) moves in a direction substantially perpendicular to the window;
  c) includes a sample biasing mechanism configured to urge the sample towards the window; and,
  b) includes:
    i) an outer cover configured to substantially surround the window; and,
    ii) a spring mounted inner cover supporting an optical surface, wherein the inner cover is configured to urge the sample against the window.

7. The apparatus according to claim 1, wherein the housing includes at least one of:
  a) a biasing mechanism that biases the cover into the closed position;
  b) an actuator to urge the cover into the open position;
  c) a handle configured to allow hand-held operation of the spectrometer; and,
  d) a mounting configured to allow the client device to be coupled to the housing.

8. The apparatus according to claim 1, wherein at least one of:
  a) the cover includes an optical surface and wherein the spectral data is at least partially indicative of radiation reflected from the optical surface; and,
  b) the cover includes an optical surface and wherein the spectral data is at least partially indicative of radiation reflected from the optical surface and the optical surface at least one of:
    i) is orientated at least one of:
      (1) substantially parallel to the window;
      (2) substantially perpendicularly to the radiation source; and
      (3) substantially perpendicularly to the sensor.
    ii) includes at least one of:
      (1) a fluoropolymer; and,
      (2) spectralon.

9. The apparatus according to claim 1, wherein one of:
  a) the sample is at least one of:
    i) plant material;
    ii) grain material;
    iii) soil material;
    iv) wheat;
    v) barley;
    vi) canola;
    vii) oats;
    viii) rice;
    ix) sorghum; and,
    x) grasses; and,
  b) the agricultural condition is indicative of at least one of:
    i) a nutrient status;
    ii) a nutrient concentration;
    iii) a nutrient deficiency;
    iv) a nutrient sufficiency;
    v) a nutrient toxicity;
    vi) a plant health status;
    vii) plant productivity;
    viii) soil health; and,
    ix) soil productivity.

10. The apparatus according to claim 1, wherein the intervention includes at least one of:
  a) at least one action to improve the agricultural condition of the agricultural environment; and,
  b) a nutrient supplement recommendation to improve the agricultural condition of the agricultural environment.

11. The apparatus according to claim 1, wherein the one or more processing devices at least one of:
  a) use the agricultural condition to at least one of:
    i) update a stored agricultural environment record for the agricultural environment;
    ii) determine future sampling locations;
    iii) determine a variable rate technology (VRT) program;
    iv) determine the intervention;
    v) determine an intervention program;
    vi) determine an intervention efficacy;
    vii) generate yield predictions; and,
    viii) generate revenue predictions;
  b) generate a representation of the indicator; and,
  c) generate a representation of the indicator including a map of the agricultural environment and indications of at least one of:
    i) agricultural conditions;
    ii) interventions;
    iii) future sampling locations; and,
    iv) predicted yields.

12. A method of determining an agricultural condition in an agricultural environment, the method including, in one or more processing devices:
  a) acquiring spectral data by measuring sample radiation at least one of reflected from and transmitted through an agricultural sample obtained from the agricultural environment;
  b) using the spectral data and at least one computational model to determine an agricultural condition in the agricultural environment, the computational model embodying relationships between the spectral data and different agricultural conditions by
    i) determining at least one metric associated with the agricultural environment by using the spectral data and a first computational model to determine the at least one metric, the first computational model embodying relationships between the spectral data and the at least one metric, wherein the first computational model is a chemometric model; and
    ii) applying the at least one metric to the at least one computational model by using the at least one metric and a second computational model to determine the agricultural condition, the second computational model embodying relationships between the at least one metric and the agricultural condition, wherein the second computational model is an agronomic model; and, c) using the agricultural condition to determine an indicator indicative of at least one of:
  i) the agricultural condition; and,
  ii) an intervention to improve the agricultural condition.

* * * * *